(12) United States Patent
Takeshima et al.

(10) Patent No.: US 7,476,525 B2
(45) Date of Patent: Jan. 13, 2009

(54) MODIFIED PYRROLOQUINOLINE QUINONE (PQQ) DEPENDENT GLUCOSE DEHYDROGENASE WITH SUPERIOR SUBSTRATE SPECIFICITY AND STABILITY

(75) Inventors: Seiji Takeshima, Tsuruga (JP); Atsushi Sogabe, Tsuruga (JP); Masanori Oka, Tsuruga (JP)

(73) Assignee: Toyo Boseki Kabushiki Kaisha, Osaka (JP)

(*) Notice: Subject to any disclaimer, the term of this patent is extended or adjusted under 35 U.S.C. 154(b) by 595 days.

(21) Appl. No.: 10/445,789

(22) Filed: May 27, 2003

(65) Prior Publication Data

US 2003/0232418 A1 Dec. 18, 2003

(30) Foreign Application Priority Data

| May 27, 2002 | (JP) | ............................. | 2002-152911 |
| May 27, 2002 | (JP) | ............................. | 2002-152913 |
| Mar. 24, 2003 | (JP) | ............................. | 2003-080244 |
| Mar. 24, 2003 | (JP) | ............................. | 2003-080310 |

(51) Int. Cl.
*C12N 9/04* (2006.01)
*C12N 1/20* (2006.01)
*C12N 15/00* (2006.01)
*C12Q 1/00* (2006.01)
*C12Q 1/32* (2006.01)
*C12P 21/04* (2006.01)
*C07H 21/04* (2006.01)
*C12Q 1/68* (2006.01)

(52) U.S. Cl. ............................. 435/190; 435/4; 435/6; 435/26; 435/69.1; 435/71.1; 435/440; 435/252.3; 435/320.1; 536/23.2

(58) Field of Classification Search ................. 435/190, 435/440, 69.1, 71.1, 252.3, 320.1; 536/23.2, 536/23.7
See application file for complete search history.

(56) References Cited

U.S. PATENT DOCUMENTS 6,103,509 A 8/2000 Sode

FOREIGN PATENT DOCUMENTS

| EP | 1 167 519 A1 | 1/2002 |
| EP | 1 176 202 A1 | 1/2002 |
| EP | 1 369 485 A1 | 12/2003 |
| JP | 10-243786 A | 9/1998 |
| JP | 11-243949 A | 9/1999 |
| JP | 2000-262281 A | 9/2000 |
| JP | 2002-312588 A | 11/2000 |
| JP | 2000-350588 A | 12/2000 |
| JP | 2001-037483 A | 2/2001 |
| JP | 2001-197853 A | 7/2001 |
| JP | 2001-346587 A | 12/2001 |
| JP | 2004-173538 A | 6/2004 |
| WO | WO 02/34919 A1 | 5/2002 |
| WO | WO 02/072839 A1 | 9/2002 |
| WO | WO 03/027294 A1 | 4/2003 |
| WO | WO 03/106668 A1 | 12/2003 |
| WO | WO 2004/005499 A1 | 1/2004 |

OTHER PUBLICATIONS

Sode et al., *FEBS Letters*, 364(3), 325-327 (1995).
Sode et al., *Biotechnology Letters*, 18(9), 997-1002 (1996).
Sode et al., *Biotechnology Letters*, 19(11), 1073-1077 (1997).
Sode et al., *Biotechnology Letters*, 21(8), 707-710 (1999).
Sode et al., *Biocatalysts and Biotransformation*, 20(6), 405-4.12 (2002).
Takahashi et al. *Electrochemistry (Tokyo)*, 68(11), 907-911 (2000).
Witarto et al., *Applied Biochemistry and Biotechnology*, 77-79, 159-168 (1999).
Yamazaki et al., *Analytical Chemistry*, 72(19), 4689-4693 (2000).
Yoshida et al., *Protein Engineering*, 12(1), 63-70 (1999).
Yoshida et al., *Biotechnology Letters*, 22 (18), 1505-1510 (2000).
Patent Abstracts of Japan (JP 2001-346587) (Dec. 18, 2001).
Database EMBL 'Online!, retrieved from EBI, Database accession No. AAZ25630, XP002254119, Toyobo Co Ltd (abstract of JP 11 243949 A) (Dec. 23, 1999).
Database EMBL 'Online!, retrieved from EBI, Database accession No. E28182, XP002254120, Toyobo Co Ltd (abstract of JP 11 243949 A) (Feb. 22, 2001).
Database EMBL 'Online!, retrieved from EBI Database accession No. E73901, XP002254121, Toyobo Co Ltd (abstract of JP 11 243949 A) (Feb. 15, 2001).
Database EMBL 'Online!, retrieved from EBI, Database accession No. AAY45178, XP002254122, Toyobo Co Ltd (abstract of JP 11 243949 A) (Dec. 23, 1999).
Igarashi et al., "Construction and Characterization of Mutant Water-Soluble PQQ Glucose Dehydrogenases with Altered Km Values—Site-Directed Mutagenesis Studies on the Putative Active Site," *Biochemical and Biophysical Research Communications*, 264 (3), 820-824 (1999).
Oubrie et al., "Active-site structure of the soluble Quinoprotein glucose dehydrogenase complexed with methylhydrazine: A covalent cofactor-inhibitor complex," *PNAS*, 96 (21), 11787-11791 (1999).
Igarashi et al., "Construction and Characterization of Mutant Water-Soluble PQQ Glucose Dehydrogenases with Altered $K_m$ Values—Site-Directed Mutagenesis Studies on the Putative Active Site," *Biochemical and Biophysical Research Communications*, 264, 820-824 (1999).
Oubrie et al. "The 1.7 Å Crystal Structure of the Apo Form of the Soluble Quinoprotein Glucose Dehydrogenase from *Acinetobacter calcoaceticus* Reveals a Novel Internal Conserved Sequence Repeat," *J. Mol. Biol.*, 289, 319-333 (1999)..

(Continued)

*Primary Examiner*—Yong D Pak
(74) *Attorney, Agent, or Firm*—Leydig, Voit & Mayer, Ltd.

(57) ABSTRACT

The present invention relates to modified pyrroloquinoline quinone dependent glucose dehydrogenase (PQQGDH) having lower activity with respect to disaccharides and/or greater stability than wild-type PQQGDH.

14 Claims, 4 Drawing Sheets

OTHER PUBLICATIONS

Oubrie et al., "Structure and mechanism of soluble quinoprotein glucose dehydrogenase," *The EMBO Journal*, 18 (19), 5187-5194 (1999).

Oubrie et al., "Structural requirements of pyrroloquinoline quinone dependent enzymatic reactions," *Protein Science*, 9, 1265-1273 (2000).

Sode et al., "Increasing the thermal stability of the water-soluble pyrroloquinoline quinone glucose Dehydrogenase by single amino acid replacement," *Enzyme and Microbial Technology*, 26, 491-496 (2000).

Bak et al. *Biochimica et Biophysica Acta*, 139: 265-276 (1967).
Bak et al. *Biochimica et Biophysica Acta*, 139: 277-293 (1967).
Bak et al. *Biochimica et Biophysica Acta*, 139: 317-327 (1967).
Bak et al. *Biochimica et Biophysica Acta*, 139: 328-335 (1967).
Branden et al., *Introduction to Protein Sturcture*, Garland Publishing Inc., p. 247 (1991).
Cleton-Jansen et al., *Journal of Bacteriology*, 170(5): 2121-2125 (May 1988).
Muller et al., *Archives of Microbiology*, 144: 151-157 (1986).

MODIFIED PYRROLOQUINOLINE QUINONE (PQQ) DEPENDENT GLUCOSE DEHYDROGENASE WITH SUPERIOR SUBSTRATE SPECIFICITY AND STABILITY

BACKGROUND OF THE INVENTION

1. Field of the Invention

The present invention relates to a modified glucose dehydrogenase (GDH) with improved substrate specificity and/or thermal stability, and more specifically to a modified PQQ-dependent glucose dehydrogenase (PQQGDH) having pyrroloquinoline quinone (PQQ) as the coenzyme, and to a manufacturing method and a glucose sensor.

The modified PQQGDH of the present invention is useful for measuring glucose in clinical assay, food analysis and the like

2. Description of the Related Art

PQQGDH is a glucose dehydrogenase having pyrroloquinoline quinone (PQQ) as its coenzyme. Because PQQGDH catalyzes a reaction in which glucose is oxidized to produce gLuconolactone, it can be used in measuring blood sugar. Blood glucose concentration is extremely important in clinical diagnosis as a marker of diabetes. at present, the principal method of measuring blood glucose employs a biosensor using glucose oxidase, but the reaction is affected by dissolved oxygen concentration, raising the possibility of errors in the measurements. attention has focused on PQQ-dependent glucose dehydrogenase as a substitute for glucose oxidase Our group discovered that the NCIMB 11517 strain of *Acinetobacter baumannii* Produces PQQ-dependent glucose dehydrogenase, conducted gene cloning and constructed a high-expression system (Japanese Patent Application Laid-Open No. H11-243949). Compared with glucose oxidase, PQQ-dependent glucose dehydrogenase had problems in substrate specificity and thermal stability.

An object of the present invention is to provide a PQQGDH with improved substrate specificity and/or thermal stability.

SUMMARY OF THE INVENTION

Figure 1:
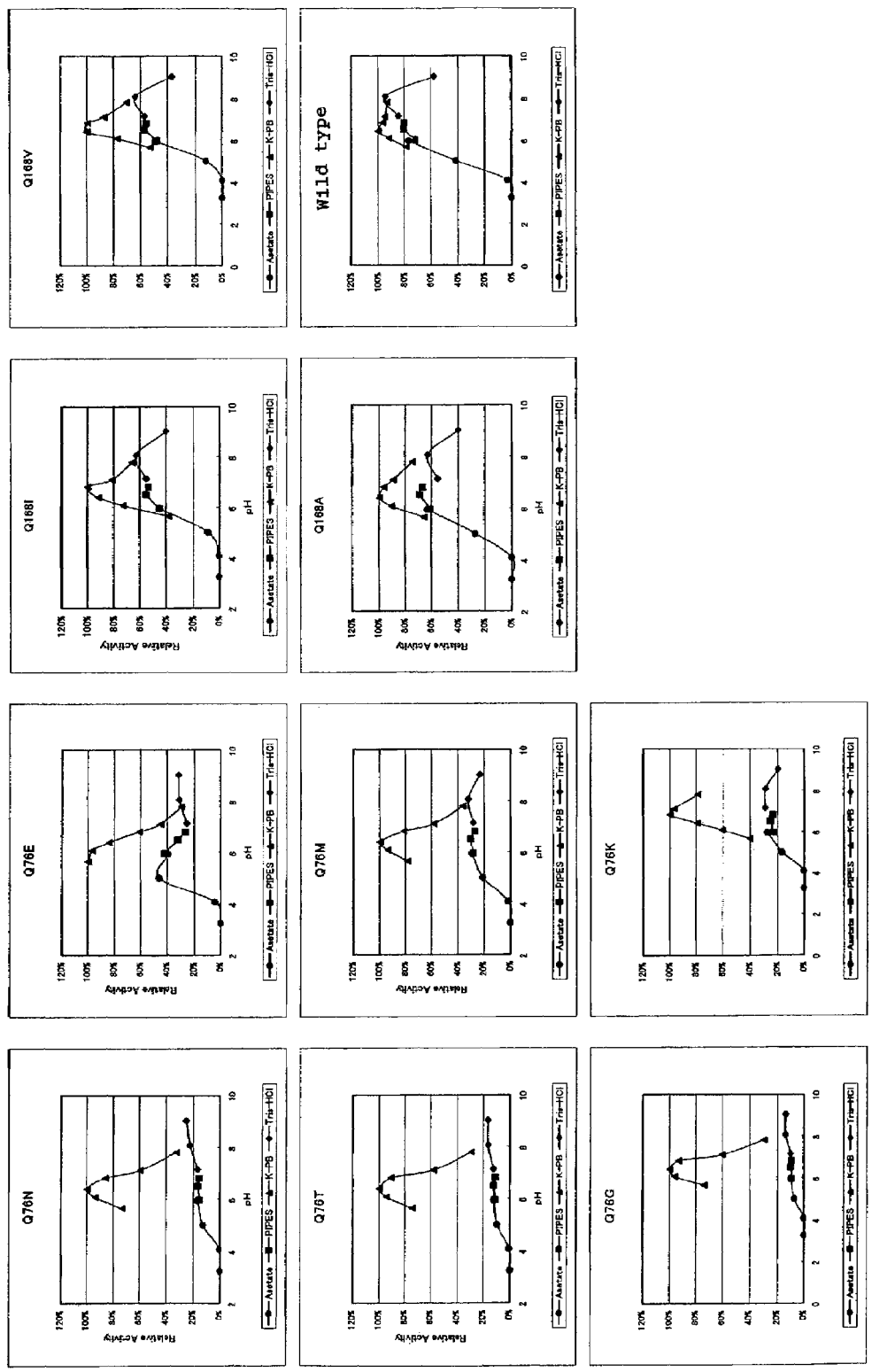
FIG. 1 shows measurement results for optimum pH.

The present invention provides a modified PQQGDH, a manufacturing method therefor, and a glucose assay kit and glucose sensor containing said PQQGDH.

1. A modified pyrroloquinoline quinone dependent glucose dehydrogenase (PQQGDH) having less activity on disaccharides and/or greater stability than wild-type PQQGDH.

2. The modified PQQGDH according to 1, wherein activity on disaccharides is less than that of wild-type glucose dehydrogenase.

3. The modified PQQGDH according to 2, wherein the disaccharide is maltose.

4. The modified PQQGDH according to 2, wherein the activity on maltose is no more , than 90% of that on glucose, 5. The modified PQQGDH according to 2, wherein the Km value for dissaccharides is increased.

6. The modified PQQGDH according to 5, wherein the dissaccharide is maltose.

7. The modified PQQGDH according to 5, wherein the Km value for maltose is 8 mM or greater.

8.the modified PQQGDH according to 2, wherein the Km value for disaccharides is greater than that for glucose.

9. The modified PQQGDH according to 8, wherein the disaccharide is maltose.

10. The modified PCQGDH according to 8, wherein the Km value for maltose is at least 1.5 times the Km value for glucose.

11. The modified PQQGDH according to 2, wherein amino acids involved in glucose binding and/or surrounding amino acids are substituted in the PQQ-dependent glucose dehydrogenase shown in SEQ ID No. 1.

12. The modified PQQGDH according to 2, wherein one or more amino acids at positions selected from the group consisting of positions 67, 68, 69, 76, 89, 167, 168, 169, 341, 342. 343, 351, 49, 174, 188, 189, 207, 215, 245, 300. 349, 129, 130 and 131 are substituted in the PQQ-dependent glucose dehydrogenase shown in SEQ ID No. 1.

13. The modified PQQGDH according to 12, wherein the amino acid substitution is selected from the group consisting of Q76N, Q76E, Q76T, Q76M, Q76G, Q76K, N167E, N167L, N167G, N167T, N167S, N167A, N167M, Q168I, Q168V, Q168A, Q168C, Q168D, Q168E, Q168F, Q168G, Q168H, Q168K, Q168L, Q168M, Q168N, Q168R, Q168S, Q168W, L169D, L169S, L169W, L169Y, L169A, L169N, L169M, L169V, L169C, L169Q, L169H, L169F, L169R, L169K, L169I , L169T, K89E, K300R, S207C, N188I , T349S, K300T, L174F, K49N, S189G, F215Y, S189G, E245D, A351P, P67K, E68K, P67D, E68T, l69C, P67R, E68R, E129R, K130G, P131G, E129N, P131T, E129Q, K130T, P131R, E129A, K130R, P131K, E341I, M342P, A343R, A343I, E341P, M342V, E341S, M342I, A343C, M342R, A+343N, L169P, L169G and L169E.

14. the modified PQQGDH according to 12, wherein the amino acid substitution is selected from the group consisting of Q76N, Q76E, Q76T, Q76M, Q76G, Q76K, Q168I, Q168V, Q168A, Q168C, Q168D, Q168E, Q168F, Q168G, Q168H, Q168K, Q168L, Q168M, Q168N, Q168R, Q168S, Q168W, (K89E+K300R), (Q168A+L169D), (Q168S+L169S), (N167E+Q168G+L169T), (N167S+Q168N+L169R), (Q168G+L169T), (N167G+Q168S+L169Y), (N167L+ Q168S+L169G), (N167G+Q168S+L169S+L174F+K49N), (Q168N+L169N+S189R), (N167E+Q168G+L169A+ S189G), (N167G+Q168R+L169A), (N167S+Q168G+ L169A), (N167G+Q168V+L169S), (N167S+Q168V+ L169S), (N167T+Q168I+L169G), (N167G+Q168W+ L169N), (N167G+Q168S+L169N), (N167G+Q168S+ L169V), (Q168R+L169C), (N167S+Q168L+L169G), (Q168C+L169S), (N167T+Q168N+L169K), (N167G+ Q168T+L169A+S207C), (N167A+Q168A+L169P), (N167G+Q168S+L169G), (N167G+Q168G), (N167G+ Q168D+L169K), (Q168P+L169G), (N167G+Q168N+ L169S), (Q168S+L169G), (N188I+T349S), (N167G+ Q168G+L169A+F215Y), (N167G+Q168T+L169G), (Q168G+L169V), (N167G+Q168V+L169T), (N167E+ Q168N+L169A), (Q168R+L169A), (N167G+Q168R), (N167G+Q168T), (N167G+Q168T+L169Q), (Q168I+ L169G+K300T), (N167G+Q168A), (N167T+Q168L+ L169K), (N167M+Q168Y+L169G), (N167E+Q168S), (N167G+Q168T+L169V+S189G), (N167G+Q168G+ L169C), (N167G+Q168K+L169D), (Q168A+L169D), (Q168S+E245D), (Q168S+L169S), (A351T), (N167S+ Q168S+L169S), (Q168I+L169Q), (N167A+Q168S+ L169S), (Q168S+L169E), (Q168A+L169G), (Q168S+

L169P), (P67K+E68K), (P67R+E68R+I69C), (P67D+E68T+I169C), (E129R+K130G+P131G), (E129Q+K130T+P131R), (E129N+P131T), (E129A+K130R+P131K), (E341L+M342P+A343R), (E341S+M342I), A343I, (E341P+M342V+A343C), (E341P+M342V+A343R), (E341L+M342R+A343N), (Q168A+L169A), (Q168A+L169C), (Q168A+L169E), (Q168A+L169F), (Q168A+L169H), (Q168A+L169I), (Q168A+L169K), (Q168A+L169M), (Q168A+L169N), (Q168A+L169P), (Q168A+L169Q), (Q168A+L169R), (Q168A+L169S), (Q168A+L169T), (Q168A+L169V), (Q168A+L169W) and (Q168A+L169Y) to improve substrate specificity.

15. The modified PQQGDH according to 2, wherein an amino acid is inserted between positions 428 and 429 in the PQQ-dependent glucose dehydrogenase shown in SEQ ID No. 1.

16. A gene coding for the modified PQQGDH according to any of 1-15.

17. A vector containing the gene according to 16.

18. A transformant transformed by the vector according to 17.

19. A method of manufactuing a modified PQQGDH, comprising cultivating the transformant according to 18.

20. A glucose assay kit comprising the modified PQQGDH according to any of 1-19.

21. A glucose sensor comprising the modified PQQGDH according to any of 1-19.

22. A modified pyrroloquinoline quinone dependent glucose dehydrogenase (PQQGDH) wherein stability is improved over that of wild-type PQQGDH.

23. The-modified PQQGDH according to 23, wherein residual activity after heat treatment at 58° C. for 30 minutes is 48% or more.

24. The modified PQQGDH according to 23, wherein residual activity after heat treatment at 58° C. for 30 minutes is 55% or more.

25. The modified PQQGDH according to 23, wherein residual activity after heat treatment at 58° C. for 30 minutes is 70% or more.

26. The modified PQQGDH according to 23, wherein one or more amino acids at positions selected from the group cosisting of positions 20, 76, 89, 168, 169, 246 and 300 are substituted in the PQQGDH shown in SEQ ID No. 1.

27. The modified PQQGDH according to 26, wherein the amino acid substitutions are selected from the group of K20E, Q76M, Q76G, K89E, Q168A, Q168D, Q168E, Q168F, Q168G, Q168H, Q168M, Q168P, Q168W, Q168Y, Q168S, L169D, L169E, L169P, L169S, Q246H, K300R, Q76N, Q76T, Q76K, L169A, L169C, L169E, L169F, L169H, L169K, L169N, L169Q, L169R, L169T, L169Y and L169G.

28. The modified PQQGDH with improved thermal stability according to 27, wherein the amino acid substitutions are selected from the group of K20E, Q76M, Q76G, (K89E+K300R), Q168A, (Q168A+L169D), (Q168S+L169S), Q246H, Q168D, Q168E, Q168F, Q168G, Q168H, Q168M, Q168P, Q168W, Q168Y, Q168S,(Q168S+L169E), (Q168S+L169P), (Q168A+L169A), (Q168A+L169C), (Q168A+L169E), (Q168A+L169F), (Q168A+L169H), (Q168A+L169K), (Q168A+L169N), (Q168A+L169P), (Q168A+L169Q), (Q168A+L169R), (Q168A+L169T), and (Q168A+L169Y)and (Q168A+L169G).

29. A gene encoding the modified PQQGDH according to any of 22-28.

30. A vector comprising the gene according to 29.

31. A transformant transformed by the vector according to 30.

32. A method of manufacturing modified PQQGDH, comprising cultivating the transformant according to 31.

33. A glucose assay kit comprising the modified PQQGDH according to any of 22-31.

34. A glucose sensor comprising the modified PQQGDH according to any of 22-31.

35. A method for determining glucose concentration in a sample using the modified PQQGDH according to any of 22-31.

36. The modified PQQGDH according to 1, which is obtained by mutation of at least one amino acid located within a range having a radius of 15 Å from an active, center of three-dimensional active structure of wild type enzyme.

37. The modified PQQGDH according to 1, which is obtained by mutation of at least one amino acid located within a range having a radius of 10 Å from a substrate in a three-dimensional active structure of wild type enzyme-substrate complex.

38. The modified PQQGDH according to 37, whose substrate is glucose.

39. The modified PQQGDH according to 1, which is obtained by mutation of at least one amino acid located within a range having a radius of 10 Å from a OH group bound to a carbon at position 1 of a substrate in a three-dimensional active structure of wild type enzyme-substrate complex.

40. The modified PQQGDH according to 39, whose substrate is glucose.

41. The modified PQQGDH according to 1, which is obtained by mutation of at least one amino acid located within a range having a radius of 10 Å from a OH group bound to a carbon at position 2 of a substrate in-a three-dimensional active structure of wild type enzyme-substrate complex.

42. The modified PQQGDH according to 41, whose substrate is glucose.

In the specification, amino acid positions are numbered beginning with 1 aspartic acid with the signal sequence removed.

The modified PQQGDH of the present invention encompasses PQQGDH having less activity on dissaccharides and/or greater thermal stability than wild-type PQQGDH.

Examples of dissaccharides include maltose, sucrose, lactose, cellobiose and the like, and particularly maltose.

Activity on disaccharides signifies the action of dehydrogenating the disaccharides.

As long as activity on disaccharides is reduced in comparison with wild-type PQQGDH, the modified PQQGDH of the present invention encompasses modified PQQGDH in which the activity on glucose Is either increased, unchanged or reduced.

In the measurement of glucose concentration, the activity on disaccharides of the modified PQQGDH of the present invention, is less than that of the case when wild-type glucose dehydrogenase is used. In the modified PQQGDH of the present invention, the activity on maltose is particularly reduced. Activity on maltose is no more than 90%, preferably 75%, more preferably 60%, particularly 40% of that of wild-type PQQGDH.

The modified PQQGDH of the present invention may have a greater Km value for disaccharides than for glucose. Modified PQQGDH having a higher Km value for maltose than for glucose is particularly desirable. The Km value for maltose should be at least 8 mM, preferably at least 12 mM, particularly at least 20 mM.

The modified PQQGDH of the present invention may be further indicated by a higher Km value for disaccharides than for glucose. Modified PQQGDH having a higher. Km value for maltose than for glucose is particularly desirable. The Km value for maltose should be at least 1.5 times or preferably at least 3 times that for glucose.

As used here, "activity on maltose" signifies the ratio of the reaction rate using glucose as a substrate to the reaction rate using disaccharides or specifically maltose as a substrate, expressed, as a percentage The degree of improvement of the invention in thermal stability expressed as residual activity after heat treatment at 58° C. for 30 minutes is preferably higher than that of wild type PQQGDH. The residual activity of the modified PQQGDH of the invention is at least 48% or preferably 55% or more preferably 70%

Examples of the modified PQQGDH with improved substrate specificity of the present invention include GDH having amino acids substituted at one or more of positions 67, 68, 69, 76, 89, 167, 168, 169, 341, 342, 343, 351, 49, 174, 188, 189, 207, 215, 245, 300, 349, 129, 130 and 131 in the amino acid sequence of SEQ ID No. 1, and GDH having an amino acids inserted between positions 428 and 429. Preferred are GDH having amino acid substitutions selected from the group consisting of Q76N, Q76E, Q76T, Q76M, Q76G, Q76K, N167E, N167L, N167G, N167T, N167S, N167A, N167M, Q168I, Q168V, Q168A, Q168C, Q168D, Q168E, Q168F, Q168G, Q168H, Q168K, Q168L, Q168M, Q168N, Q168R, Q168S, Q168W, L169D, L169S, L169W, L169Y, L169A, L169N, L169M, L169V, L169C, L169Q, L169H, L169F, L169R, L169K, L169I, L169T, K89E, K300R, S207C, N188I, T349S, K300T, L174F, K49N, S189G, F215Y, S189G, E245D, A351T, P67K, E68K, P67D, E68T, 169C, P67R, E68R, E129R, K130G, P131G, E129N, P131T, E129Q, K130T, P131R, E129A, K130R, P131K, E341L, M342P, A343R, A+343I, E341P, M342V, E341S, M342I, A343C, M342R, A343N, L169P, L169G and L169E, and GDH having L, A or K inserted between positions 428 and 429. Substitutions at positions 67, 68, 69, 76, 89, 167, 168, 169, 341, 342, 343, 351, 49, 174, 188, 189, 207, 215, 245, 300, 349, 129, 130 and-131 may be at one position or multiple positions.

As used here, "Q76N" signifies the substitution of N (A+Sn) for Q (G+Ln) at position 76.

Substitutions of Q76N, Q76E, Q76T, Q76M, Q76G, Q76K, Q168I, Q168V, Q168A, (N167E+Q168G+L169T), (N167S+Q168N+L169R), (Q168G+L169T), (N167G+Q168S+L169Y), (N167L+Q168S+L169G), (N167G+Q168S+L169S +L174F+K49N), (Q168N+L169N+S198R). (N167E+Q168G+L169A+S189G), (N167G+Q168R+L169A), (N167S+Q168G+L169A), (N167G+Q168V+L169S), (N167S+Q168V+L169S), (N167T+Q168I+L169G), (N167G+Q168 W+L169N), (N167G+Q168S+L169N), (N167G+Q168S+L169V), (Q168R+L169C), (N167S+Q168L+L169G), (Q168C+L169S), (N167T+Q168N+L169K), (N167G+Q168T+L 169A+S207C), (N167A+Q168A+L169P), (N167G+Q168S+L169G), (N167G+Q168G), (N167G+Q168D+L169K), (Q168P+L169G), (N167G+Q168N+L169S), (Q168S+L169G), (N188I+T349S), (N167G+Q168G+L169A+F215Y), (N167G+Q168T+L169G), (Q168G+L169V), (N167G+Q168V+L169T), (N167E+Q168N+L169A), (Q168R+L169A), (N167G+Q168R), (N167G+Q168T), (N167G+Q168T+L169Q), (Q168I+L 169G+K300T), (N167G+Q168A), (N167T+Q168L+L169K), (N167M+Q168Y+L169G), (N 167E+Q168S), (N167G+Q168T+L169V+S189G), (N167G+Q168G+L169C), (Q168A+L169D), (Q168S+E245D), (Q168S+L69S), (A351T), (N167G+Q168S+L169S), (Q168I+L169Q), (N167A+Q168S+L169S), (Q168S+L169E), (Q168A+L169G), (Q168S+L169P), (P67K+E68K), (P67R+E68R+I169C), (P67D+E68T+I69C), (E129R+K130G+P131G), (E129Q+K130T+P131R), (E129N+P131T), (E129A+K130R+P131K), (E341L+M342P+A343R), (E34 1S+M342I), A343I (E341P+M342V+A343C), (E341P+M342V+A343R), (E341L+M342R+A343N), (Q168A+L169A), (Q168A+L169C), (Q168A+L169E), (Q168A+L169F), (Q168A+L169H), (Q168A+L169I), (Q168A+L169K), (Q168A+L169M), (Q168A+L169N), (Q168A+L169P), (Q168A+L169Q), (Q168A+L169R), (Q168A+L169S), (Q168A+L169T), (Q168A+L169V), (Q168A+L169W) and (Q168A+L169Y), and also insertion of L, A or K between positions 428 and 429 contribute to improving the substrate specificity of PQQGDH. As used here, substrate specificity signifies the ratio (%) of the reaction rate with glucose as the substrate to the reaction rate with disaccharides (particularly maltose) used as the substrate.

The PQQGDH of the present invention with improved thermal stability has amino acid substitutions at one or more of positions 20, 76, 89, 168, 169, 246 and 300 of the amino acid sequence of SEQ ID No. 1, and preferably has amino acid substitutions selected from the group consisting of K20E, Q76M, Q76G, K89E, Q168A, Q168D, Q168E, Q168F, Q168G, Q168H, Q168M, Q168P, Q168W, Q168Y, Q168S, L169V, L169E, L169P, L169S, Q246H, K300R, Q76N, Q76T, Q76K, L169A, L169C, L169E, L169F, L169H, L169K, L169N, L169Q, L169R, L169T, L169Y and L169G. Substitutions at positions 20, 76, 89, 168, 169, 246 and 300 may be at one position or multiple positions.

As used here "K20E" signifies that K (Lys) has been replaced with E (Glu) at position 20.

The amino acid substitutions K20E, Q76M, Q76G, (K89E+K300R), Q168A, (Q168A+L169D), (Q168S+L169S), Q246H, Q168D, Q168E, Q168F, Q168G, Q168H, Q168M, Q168P, Q168W, Q168Y, Q168S, (Q168S+L169E), (Q168S+L169P), (Q168A+L169A), (0168A+L169C), (Q168A+L169E), (Q168A+L169F), (Q168A+L169H), (Q168A+L169K), (Q168A+L169N), (Q168A+L169P), (Q168A+L169Q), (Q168A+L169R), (Q168A+L169T), and (Q168A+L169Y) and (Q168A+L169G) contribute particularly to the thermal stability of the PQQGDH.

The wild-type PQQGDH protein for modification shown in SEQ ID No. 1 and the nucleotide sequence shown in SEQ ID No. 2 are both well known, and are disclosed in Japanese Patent Application Laid-Open No. H11-243949.

There are no particular limits on the method of manufacturing the modified protein of the present invention, which may be manufactured according to the procedures shown below. Commonly used methods of modifying genetic information may be used in modifying the amino acid sequence which constitutes the protein. That is, DNA having the genetic information of the modified protein is created by replacing a specific nucleotide or nucleotides in DNA having the genetic information for the protein, or by inserting or deleting a specific nucleotide or nucleotides. Actual methods of replacing one or more nucleotides in DNA include those employing commercial kits (such as the Clonetech Transformer Mutagenesis Kit; Stratagene EXOIII/Mung Bean Deletion Kit; or Stratagene QuickChange Site Directed Mutagenesis Kit), or those employing the polymerase chain reaction (PCR).

The resulting DNA having the genetic information of the modified protein is linked to a Plasmid and inserted into a host cell or microorganism to create a transformant which produces the modified protein. Plasmids which can be used include pbluescript, pUC18 or the like for example if *Escherichia coli* is the host microorganism. Host organisms which can be used include for example *Escherichia coli* W3110, *Escherichia coli* C600, *Escherichia coli* JM109, *Escherichia coli* DH5α and the like. Insertion of the vector into the host organism may be accomplished for example by introducing the recombinant DNA in the presence of calcium ions when the host organism is of the genus *Escherichia*, and the electroporation method may also be used. Commercially available competent cells (such as Toyobo Competent High JM109) can also be used.

The resulting transformant reliably produces large quantities of the modified protein when cultured in a nutrient medium. The culture conditions for the transformant can be selected according to the physiological requirements of the host; a liquid culture is normally used, but for industrial puposes an aerated agitation culture is advantageous. A wide range of nutrients which are ordinarily used in culturing the organism can be used in the medium. The carbon source may be any convertible carbon compound, including for example glucose, sucrose, lactose, maltose, fructose, molasses and pyruvic acid. The nitrogen source may be any usable nitrogen compound, including for example peptone, meat extract, yeast extract, hydrolyzed casein and soybean meal alkali extract. In addition, phosphates, carbonates, sulfates, salts of magnesium, calcium, potassium, iron, manganese, zinc and the like, specific amino acids and specific vitamins are used as necessary. The culture temperature can be adjusted within the range at which the organism grows and produces the modified protein, but should be about 20-42° C. in the case of *Escherichia coli*. The culture time will vary somewhat depending on conditions: the culture can be terminated at a suitable point according to when the maximum yield of the modified protein is obtained, with the normal time range being 6-48 hours. The pH of the culture medium can be varied within the range at which the organism grows and produces the modified protein, with a pH of 6.0-9.0 being particularly desirable.

Culture medium containing organisms which produce the modified protein can be collected from the culture and used as is, but ordinarily when the modified protein is present in the culture medium a solution containing the modified protein is isolated from the bacterial cells by conventional means such as filtration or centrifugation for purposes of use. When the modified protein is present in the cells, they are harvested from the resulting culture by methods such as filtration or centrifugation, the cells are broken down by mechanical methods or enzymatic methods such as lysozyme, and the modified protein is solubilized as necessary by the addition of a chelating agent such as EDTA and/or a surfactant and isolated and harvested as an aqueous solution.

The resulting solution containing the modified protein can then be subjected to vacuum concentration, membrane concentration and salting out with ammonium sulfate or sodium sulfate or else precipitation by fractional precipitation using a hydrophilic organic solvent such as methanol, ethanol or acetone. Heat treatment and isoelectric treatment are also effective means of purification. The purified modified protein can be obtained by gel filtration with an adsorbent or gel filter, adsorption chromatography, ion exchange chromatography or affinity chromatography.

In the present invention, we were able to obtain modified PQQGDH with improved substrate specificity by focusing on the 76, 167, 168 and 169 Positions of the PQQGDH shown in SEQ ID No. 1 and creating amino acid substitutions for them. The substitutions Q76K, Q168A, (Q168S+L169S), (Q168A+L169D), (Q168S+E245D), (Q168S+L169E), (Q168A+L169G), (Q168S+L169P), (Q168A+L169A), (Q168A+L169C), (Q168A+L169E), (Q168A+L169K), (Q168A+L169M), (Q168A+L169N), (Q168A+L169P), (Q168A+L169S) and (Q168A+L169T) are-particularly desirable in terms of substrate specificity.

In the present invention, we were able to obtain modified PQQGDH with improved stability by focusing on the 20, 76, 89, 168, 169, 246 and 300 Positions of the PQQGDH shown in SEQ ID No. 1 and creating amino acid substitutions for them. The substitutions K20E, (K89E+K300R), Q168A, (Q168A+L169D), (Q168S+L169S), (Q168S+L169E), (Q168S+L169P), (Q168A+L169G), Q168D, Q168E, Q168F, Q168G, Q168H, Q168M, Q168P, Q168S, Q168W, Q168Y, (Q168A+L169A), (Q168A+L169C), (Q168A+L169E), (Q168A+L169F), (Q168A+L169H), (Q168A+L169K), (Q168A+L169N), (Q168A+L169P), (Q168A+L169Q), (Q168A+L169R), (Q168A+L169T), (Q168A+L169Y) and Q246H are particularly desirable in terms of thermal stability.

Glucose Assay Kit

The present invention also provides a glucose assay kit containing modified PQQGDH according to the present invention. The glucose assay kit of the present invention contains enough modified PQQGDH according to the invention for at least one assay. Typically the kit contains in addition to the modified PQQGDH of the invention such buffers, mediators, standard glucose solutions for making calibration curves, and instructions for use are needed to perform the assay. The modified PQQGDH according to the invention can be provided in a variety of forms such as for example a freeze-dried reagent or a solution in a suitable storage solution. The modified PQQGDH of the present invention is preferably provided as a holoenzyme, but may also be provided as an apoenzyme and converted at the time of use.

Glucose Sensor

The present invention also provides a glucose sensor which uses modified PQQGDH according to the invention A carbon, gold or platinum electrode or the like is used as the electrode, with the enzyme of the present invention being immobilized on the electrode. Possible immobilizing methods include those employing crosslinking reagents, enclosure in a polymer matrix, coating with a dialysis membrane, employing photocrosslinked polymers, conductive polymers, and oxidation-reduction polymers, as well as adsorption fixing on the electrode or fixing in a polymer together with an electron mediator typified by ferrocene and its derivatives, and a combination of these may also be used. Preferably the modified PQQGDH of the present invention is immobilized on the electrode as a holoenzyme, but it may also be immobilized as an apoenzyme, and PQQ supplied in solution or as a sparate layer. Typically the modified PQQGDH of the invention is first immobilized on a carbon electrode using gLutaraldehyde, and the gLutaraldehyde is then blocked by treatment with a reagent having an amine group.

Glucose concentration can be measured as follows. Buffer is placed in a thermostatic cell and maintained at a constant temperature after the addition of PQQ, $CaCl_2$ and a mediator. Mediators that can be used Include potassium ferricyanide, phenazine methosulfate and the like. An electrode on which the modified PQQGDH of the present invention has been immobilized is used as the work electrode, together with a counter electrode (such as a platinum electrode) and a reference electrode (such as an Ag/AgCl electrode). A fixed voltage is applied to the carbon electrode, and once the current has stabilized a sample containing glucose is added and the increase in current measured. The glucose concentration in the sample can then be calculated based on a calibration curve prepared from glucose solutions with standard-concentration.

BEST MODE FOR CARRYING OUT THE INVENTION

EXAMPLE 1

Construction of an Expression Plasmid with PQQ-dependent Glucose Dehydrogenase Gene Expression plasmid pNPG5 For wild type PQQ-dependent glucose dehydrogenase is the pBluescript SK(−) vector with a structural gene encoding PQQ-dependent glucose dehydrogenase derived from *Acinetobacter baumannii* NCIMB 11517 strain inserted in the multicloning site Its nucleotide sequence is shown in SEQ ID No. 2 in the sequence listing, while the amino acid sequence of PQQ-dependent glucose dehydrogenase as inferred from this sequence is shown as SEQ ID No. 1.

EXAMPLE 2

Manufacture of Modified PQQ-dependent Glucose Dehydrogenase

Based on recombinant plasmid pNPG5 containing the wild-type PQQ-dependent glucose dehydrogenase gene, together with, the synthetic oligonucleotide shown in SEQ ID No. 3 and its complementary synthetic oligonucleotide, a mutation treatment was carried out using a QuickChange™ Site-Directed Mutagenesis Kit (Stratagene) according to the kit's protocols, the nucleotide sequence was then determined to obtain a recombinant plasmid (pNPG5M1) carrying a gene encoding modified PQQ-dependent glucose dehydrogenase in which glutamine at 76th position is replaced by asparagine in the amino acid sequence shown in SEQ ID No. 2.

Based on pNPG5 and the synthetic oligonucleotide shown in SEQ ID No. 4 and its complementary synthetic oligonucleotide, a recombinant plasmid (pNPG5M2) carrying a gene encoding modified PQQ-dependent glucose dehydrogenase in which glutamine at 76th position is replaced by glutamic acid in the amino acid sequence shown in SEQ ID No 2 was obtained by methods similar to those described above.

Based on pNPG5 and the synthetic oligonucleotide shown in SEQ ID No. 5 and its complementary synthetic oligonucleotide, a recombinant plasmid (pNPG5M3) carrying a gene encoding modified PQQ-dependent glucose dehydrogenase in which glutamine at 76th position is replaced by threonine in the amino acid sequence shown in SEQ ID No. 2 was obtained by methods similar to those described above.

Based on pNPG5 and the synthetic oligonucleotide shown in SEQ ID No. 6 and its complementary synthetic oligonucleotide, a recombinant plasmid (pNPG5M4) carrying a gene encoding modified PQQ-dependent glucose dehydrogenase in which glutamine at 76th position is replaced by methionine in the amino acid sequence shown in SEQ ID No. 2 was obtained by methods similar to those described above.

Based on pNPG5 and the synthetic oligonucleotide shown in SEQ ID No. 7 and its complementary synthetic oligonucleotide, a recombinant plasmid (pNPG5M5) carrying a gene encoding modified PQQ-dependent glucose dehydrogenase in which glutamine at 76th position is replaced by glycine in the amino acid sequence shown in SEQ ID No. 2 was obtained by methods similar to those described above.

Based on pNPG5 and the synthetic oligonucleotide shown in SEQ ID No. 8 and its complementary synthetic oligonucleotide, a recombinant plasmid (pNPG5M6) carrying a gene encoding modified PQQ-dependent glucose dehydrogenase in which glutamine at 76th position is replaced by lysine in the amino acid sequence shown in SEQ ID No. 2 was obtained by methods similar to those described above.

Based on pNPG5 and the synthetic oligonucleotide shown in SEQ ID No. 9 and its complementary synthetic oligonucleotide, a recombinant plasmid (pNPG5M7) carrying a gene encoding modified PQQ-dependent glucose dehydrogenase in which glutamine at 168th position is replaced by isoleucine in the amino acid sequence shown in SEQ ID No. 2 was obtained by methods similar to those described above.

Based on pNPG5 and the synthetic oligonucleotide shown in SEQ ID No. 10 and its complementary synthetic oligonucleotide, a recombinant plasmid (pNPG5M8) carrying a gene encoding modified PQQ-dependent glucose dehydrogenase in which glutamine at 168th position is replaced by valine in the amino acid sequence shown in SEQ ID No. 2 was obtained by methods similar to those described above.

Based on pNPG5 and the synthetic oligonucleotide shown in SEQ ID No. 11 and its complementary synthetic oligonucleotide, a recombinant plasmid (pNPG5M9) carrying a gene encoding modified PQQ-dependent glucose dehydrogenase in which glutamine at 168th position is replaced by alanine in the amino acid sequence shown in SEQ ID No. 2 was obtained by methods similar to those described above.

Based on pNPG5 and the synthetic oligonucleotide shown in SEQ ID No. 22 and its complementary synthetic oligonucleotide, a recombinant plasmid (pNPG5M10) carrying a gene encoding modified PQQ-dependent glucose dehydrogenase in which lysine at 20th position is replaced by glutamic acid in the amino acid sequence shown in SEQ ID No. 2 was obtained by methods similar to those described above.

Based on pNPG5 and the synthetic oligonucleotide shown in SEQ ID No. 23 and its complementary synthetic oligonucleotide, a recombinant plasmid carrying a gene encoding modified PQQ-dependent glucose dehydrogenase in which lysine at 89th position is, replaced by glutamic acid in the amino acid sequence shown in SEQ ID No. 2 was obtained by methods similar to those described above. Subsequently, based on the plasmid and the synthetic oligonucleotide shown in SEQ ID No. 24 and its complementary synthetic oligonucleotide, a recombinant plasmid (pNPG5M11) carrying a gene encoding modified PQQ-dependent glucose dehydrogenase in which lysine at 89th position is replaced by glutamic acid and also lysine at 300th position is replaced by arginine in the amino acid sequence shown in SEQ ID No. 2 was obtained by methods similar to those described above.

Based on pNPG5 and the synthetic oligonucleotide shown in SEQ ID No. 25 and its complementary synthetic oligonucleotide, a recombinant plasmid (pNPG5M12) carrying a gene encoding modified PQQ-dependent glucose dehydrogenase in which glutamine at 246th position is replaced by histidine in the amino acid sequence shown in SEQ ID No. 2 was obtained by methods similar to those described above.

Based on pNPG5 and the synthetic oligonucleotide shown in SEQ ID No. 26 and its complementary synthetic oligonucleotide, a recombinant plasmid (pNPG5M13) carrying a gene encoding modified PQQ-dependent glucose dehydrogenase in which glutamine at 168th position is replaced by serine and leucine at 169th position is replaced by serine in the amino acid sequence shown in SEQ ID No. 2 was obtained by methods similar to those described above.

Based on pNPG5 and the synthetic oligonucleotide shown in SEQ ID No. 27 and its complementary synthetic oligonucleotide, a recombinant plasmid (pNPG5M14) carrying a gene encoding modified PQQ-dependent glucose dehydrogenase in which glutamine at 168th position is replaced by alanine and leucine at 169th position is replaced by aspartic acid in the amino acid sequence shown in SEQ ID No. 2 was obtained by methods similar to those described above.

Based on pNPG5 and the synthetic oligonucleotide shown in SEQ ID No. 66 and its complementary synthetic oligonucleotide, a recombinant plasmid (pNPG5M15) carrying a gene encoding modified PQQ-dependent glucose dehydrogenase in which glutamine at 168th position is replaced by serine and leucine at 169th position is replaced by glutamic acid in the amino acid sequence shown in SEQ ID No. 2 was obtained by methods similar to those described above.

Based on pNPG5 and the synthetic oligonucleotide shown in SEQ ID No. 67 and its complementary synthetic oligonucleotide, a recombinant plasmid (pNPG5M16) carrying a gene encoding modified PQQ-dependent glucose dehydrogenase in which glutamine at 168th position is replaced by serine and leucine at 169th position is replaced by proline in the amino acid sequence shown in SEQ ID No. 2 was obtained by methods similar to those described above.

Based on pNPG5 and the synthetic oligonucleotide shown in SEQ ID No. 68 and its complementary synthetic oligonucleotide, a recombinant plasmid (pNPG5M17) carrying a gene encoding modified PQQ-dependent glucose dehydrogenase in which glutamine at 168th position is replaced by alanine and leucine at 169th position is replaced by glycine in the amino acid sequence shown in SEQ ID No. 2 was obtained by methods similar to those described above.

E. coli competent cells (Escherichia coli JM109, Toyobo) were transformed using the recombinant plasmids pNPG5, pNPG5M1, PNPG5M2, pNPG5M3, pNPG5M4, pNPG5M5, pNPG5M6, pNPG5M7, pNPG5M8, pNPG5M9, pNPG5M10, pNPG5M11, pNPG5M12, pNPG5M13, pNPG5M14, pNPG5M15, pNPG5M16 and pNPG5M17 to obtain the respective transformants.

EXAMPLE 3

Construction of Expression Vectors which can be Replicated in Pseudomonas Bacteria 5 μg of the DNA of the recombinant plasmid pNPG5M1 obtained in Example 2 was cleaved with restriction enzymes BamHI and XhoI (Toyobo), and the structural gene area of mutated PQQ-dependent glucose dehydrogenase was isolated. The isolated DNA together with 1 μg of pTM33 cleaved with BamHI and XhoI was reacted at 16° C. for 16 hours with 1 unit of T4 DNA ligase to ligate the DNAs. The ligated DNA was then transformed using competent cells of E. coli DH5α. The resulting expression plasmid was named pNPG6M1.

Expression plasmids were obtained by the same methods using the recombinant plasmids pNPG5, pNPG5M2, pNPG5M3, pNPG5M4, pNPG5M5, pNPG5M6, pNPG5M7, pNPG5M8, pNPG5M9, pNPG5M10, pNPG5M11, pNPG5M12, pNPG5M13, pNPG5M14 pNPG5M15, pNPG5M16 and pNPG5M17. The resulting expression plasmids were named pNPG6, pNPG6M2, pNPG6M3, pNPG6M4, pNPG6M5, pNPG6M6, pNPG6M7, pNPG6M8, pNPG6M9, pNPG6M10, pNPG6M11, pNPG6M12, pNPG6M13, pNPG6M14, pNPG6M15, pNPG6M16 and pNPG6M17.

EXAMPLE 4

Preparation of Transformant of Pseudomonas Bacteria

*Pseudomonas putida* TE3493 (International Patent Organism Depositary (IPOD) Accession No. 11298) was cultured for 16 hours at 30° C. in LBG medium (LB medium+0.3% Glycerol), the cells were collected by centrifugation (12,000 rpm, 10 Minutes), and 8 ml of a chilled 5 mM K-phosphate buffer (pH 7.0) containing 300 mM sucrose was added to the cells to suspend the cells. The cells were collected again by centrifugation (12,000 rpm, 10 minutes), and 0.4 ml of a chilled 5 mM K-phosphate buffer (pH 7.0) containing 300 mM sucrose was added to the cells to suspend the cells.

0.5 μg of the expression plasmid pNPG6M1 obtained in Example 3 was added to this suspension, and transformation was carried out by electroporation. The target transformant was obtained from a colony grown in LB agar medium containing 100 μg/ml of streptomycin.

Transformants were obtained respectively by the same methods from the expression plasmids named pNPG6, pNPG6M2, pNPG6M3, pNPG6M4, pNPG6M5, pUPG6M6, pNPG6M7, pNPG6M8, pNPG6M9, pNPG6M10, pNPG6M11, pNPG6M12, pNPG6M13, pNPG6M14, pNPG6M15, pNPG6M16 and pNPG6M17.

TEST EXAMPLE 1

Measurement of GDH Activity (1) Measurement Principles

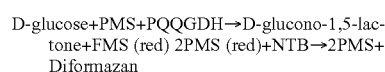

D-glucose+PMS+PQQGDH→D-glucono-1,5-lactone+FMS (red) 2PMS (red)+NTB→2PMS+Diformazan The presence of diformazan formed by reduction of nitrotetrazoliun blue (NTB) with phenazine methosulfate (PMS) (red) was measured by spectrophotometry at 570 nm.

(2) Definition of Units 1 unit is defined as the amount of PQQGDH enzyme needed to form 0.5 Millimoles of diformazan per minute under the conditions described below.

(3) Methods

Reagents

A. D-glucose solution: 0.5 M (0.9 G D-glucose (molecular weight 180.16)/10 ml $H_2O$)

B. PIPES-NaOH buffer, pH 6.5: 50 mM (1.51 G of PIPES (molecular weight 302.36) suspended in 60 ml water was dissolved in 5N NaOH, and 2.2 ml of 10% Triton X-100 was added pH was adjusted to 6.5±0.05 at 25° C. using 5N NaOH, and water was added to a total of 100 ml.)

C. PMS solution: 3.0 mM (9.19R mg phenazine methosulfate (molecular weight.817.65)/10 ml $H_2O$)

D. NTB solution: 6.6 mM (53.96 Mg nitrotetrazolium blue (molecular weight 817.65)/10 ml $H_2O$)

E. Enzyme diluent: 50 mM PIPES-NaOH buffer (pH 6.5) containing 1 mM $CaCl_2$, 0.1%Triton X-100 and 0.1% BSA Procedures 1. The following reaction mixture was prepared in a shaded bottle, and stored on ice (prepared when needed)

| 1.8 ml | D-glucose solution | (A) |
| 24.6 ml | PIPES-NaOH buffer (pH 6.5) | (B) |
| 2.0 ml | PMS solution | (C) |
| 1.0 ml | NTB solution | (D) |

TABLE 1

| Concentration in the assay mixture | |
|---|---|
| PIPES buffer | 42 mM |
| D-glucose | 30 mM |
| PMS | 0.20 mM |
| NTB | 0.22 mM |

2. A plastic test tube filled with 3.0 ml of the reaction mixture was pre-heated for 5 minutes at 37° C.
3. 0.1 ml of enzyme solution was added and mixed by gentle inversion.
4. The increase in absorbance over water was recorded for 4-5 minutes on a spectrophotometer at 570 nm with the temperature maintained at 37° C. to calculate ΔOD per minute from the initial straight-line segment of the curve (OD test).

at the same time, the same methods were repeated except that enzyme diluent (E) was added in place of the enzyme solution, and the blank (ΔOD blank) was measured.

Immediately before the assay, enzyme powder was dissolved in chilled enzyme diluent (E), and diluted to 0.1-0.8 U/ml in the same buffer (a plastic tube is preferred because of the adhesiveness of the enzyme).

Calculations
Activity was calculated using the following equation:

$$U/ml = \{\Delta OD/min\ (\Delta OD\ test - \Delta OD\ blank) \times Vt \times df\} / (20.1 \times 1.0 \times Vs)$$

$$U/mg = (U/ml) \times 1/C$$

Vt: Total volume (3.1 ml)
Vs: Sample volume (1.0 ml)
20.1: ½ millimole molecular extinction coefficient of Diformazan
1.0: Optical path length (cm)
df: Dilution factor
C: Enzyme concentration in the solution (c mg/ml)

Preparation of Holo-Expressive Purified Enzyme 500 ml of Terrific broth was taken in a 2 volume Sakaguchi flask, autoclaved for 20 minutes at 121° C. and left to cool, after which streptomycin which had been separately sterile-filtered was added to a final concentration of 100 μg/ml. This medium was then inoculated with 5 ml of a culture solution of *Pseudomonas putida* TE3493(pNPG6M1) which had been first cultured for 24 hours at 30° C. in a PY medium containing 100 μg/ml of streptomycin, and aeration agitation cultured for 40 hours at 30° C. PQQ-dependent glucose dehydrogenase activity upon completion of the culture was about 120 U/ml per 1 ml of culture solution as measured by the methods described above.

The aforementioned cells were collected by centrifugation, suspended in a 20 mM phosphate buffer (pH 7.0), broken up with ultrasonication and re-centrifuged, and the supernatant was taken as crude enzyme solution. This crude enzyme solution thus obtained was isolated and purified by HiTrap-SP (Amersham Pharmacia) ion exchange column chromatography. After dialysis with a 10 mM PIPES-NaOH buffer (pH 6.5), calcium chloride was added to a final concentration of 1 mM. Finally, isolation and purification were performed by HiTrap-DEAE (Amersham Pharmacia) ion exchange column chromatography to obtain the purified enzyme sample. The sample obtained by these methods exhibited a generally single SDS-PAGE band.

Purified enzyme products were also obtained by the same methods for the *Pseudomonas putida* TE3493 transformants of pNPG6, pNPG6M2, pNPG6M3, pNPG6M4, pNPG6M5, pNPG6M6, pNPG6M7, pNPG6M8, pNPG6M9, pNPG6M10, PNPG6M11, pNPG6M12, pNPG6M13, pNPG6M14, pNPG6M15, pNPG6M16 and pNPG6M17.

The resulting purified enzymes were used in evaluating properties.

Measurement of Km Value

PQQGDH activity was measured according to the aforementioned activity measurement method. The Km value for glucose was measured by altering the substrate concentration in the aforementioned activity measurement method. The Km value for maltose was measured by substituting a maltose solution for the glucose solution in the aforementioned activity measurement method, and altering the substrate concentration as when measuring the Km value for glucose. The results are shown in Tables 2A, 2B, 6, 9 and 14.

Substrate Specificity

PQQGDH activity was measured according to the aforementioned activity measurement method. Using glucose as the substrate solution and maltose as the substrate solution, the respective dehydrogenase activity values were measured, and the relative value was calculated with 100 given as the measurement value using glucose as the substrate. In the case of dehydrogenase activity using maltose as the substrate solution, a 0.5M maltose solution was prepared and used for measuring activity. The results are shown in Tables 2A, 2B, 4, 5, 6, 8, 9, 11, 13 and 14.

Measurement of Thermal Stability

The various kinds of PQQGDH were stored in buffer (10 mM PIPES-NaOH (p16.5) containing 1 mM $CaCl_2$ and 1 AM PQQ) with an enzyme concentration of 5 U/ml, and residual activity was measured after heat treatment at 58° C. The results are shown in Tables 2A, 2B, 6, 9 and 14. The heat treatment was conducted for 20 minutes with respect to Table 2B and for 30 minutes with respect to heat treatment assays other than Table 2B.

Measurement of Optimum pH

Enzyme activity was measured in a 50 mM phosphate buffer (pH 5.0-8.0) containing 0.22% Triton-X100, a 50 mM acetate buffer (pH 3.0-6.0) containing 0.22% Triton-X100, a 50 mM PIPES-NaOH buffer (pH 6.0-7.0) containing 0.22% Triton-X100, and a 50 mM Tris-HCl buffer (pH 7.0-9.0) containing 0.22% Triton-X100. The results are shown in FIG. 1. The pH values that produced the highest activity are given in Table 2A.

TABLE 2A

| Mutation | Specific activity | Substrate specificity | Km (Mal) | Km (Glc) | Optimum pH | Thermal stability |
|---|---|---|---|---|---|---|
| Q76N | 49 | 66% | 13.6 | 3.1 | 6.4 | 49.1% |
| Q76E | 36 | 68% | 13.6 | 3.7 | 5.6 | 42.5% |
| Q76T | 32 | 84% | 10.3 | 2.5 | 6.4 | 49.0% |
| Q76M | 108 | 81% | 8.7 | 2.2 | 6.4 | 55.3% |
| Q76G | 32 | 84% | 10.6 | 2.2 | 6.4 | 58.5% |
| Q76K | 84 | 32% | 29.9 | 7.9 | 6.8 | 48.4% |
| Q168I | 231 | 69% | 11.9 | 5.3 | 6.8 | 27.3% |
| Q168V | 377 | 71% | 13.0 | 6.4 | 6.4 | 32.2% |
| Q168A | 333 | 37% | 35.3 | 10.4 | 6.4 | 59.2% |
| Wild type | 1469 | 103% | 4.1 | 6.5 | 6.4 | 46.7% |

Notes)
Specific activity: Enzyme activity (U/ml)/A280 nm absorbance (ABS)
Km (Mal): Kin value (mM) for maltose
Km (Glc): Km value (mM) for glucose

TABLE 2B

| Mutation | Specific activity | Substrate specificity | Thermal stability |
|---|---|---|---|
| K20E | 924 | 105% | 49.7% |
| K89E + K300R | 1038 | 81% | 58.8% |
| Q246H | 686 | 192% | 82.2% |
| Q168S + L169S | 288 | 33% | 73.0% |
| Q168A + L169D | 106 | 18% | 78.8% |
| Q168S + L169E | 270 | 19% | 47.0% |
| Q168S + L169P | 460 | 25% | 47.2% |
| Q168A + L169G | 170 | 18% | 78.3% |
| Wild type | 1469 | 103% | 43.4% |

Note)
Specific activity: Enzyme activity (U/ml)/A280 nm absorbance (ABS)

Confirmation of glucose assayability of Q76K

The following reaction reagent was prepared containing 0.45 U/ml of Q76K.

| 50 mM | PIPES-NaOH buffer (pH 6.5) |
|---|---|
| 1 mM | CaCl$_2$ |
| 0.22% | Triton-X100 |
| 0.4 mM | PMS |
| 0.26 mM | WST-1 (water-soluble tetrazolium salt, Dojin Kagaku) |

According to the methods described below for measuring glucose, purified water, 100 Mg/dl standard solution and 10-level dilution series of aqueous glucose solution (600 mg/dl) were measured as sample, and linearity was confirmed.

Figure 2:
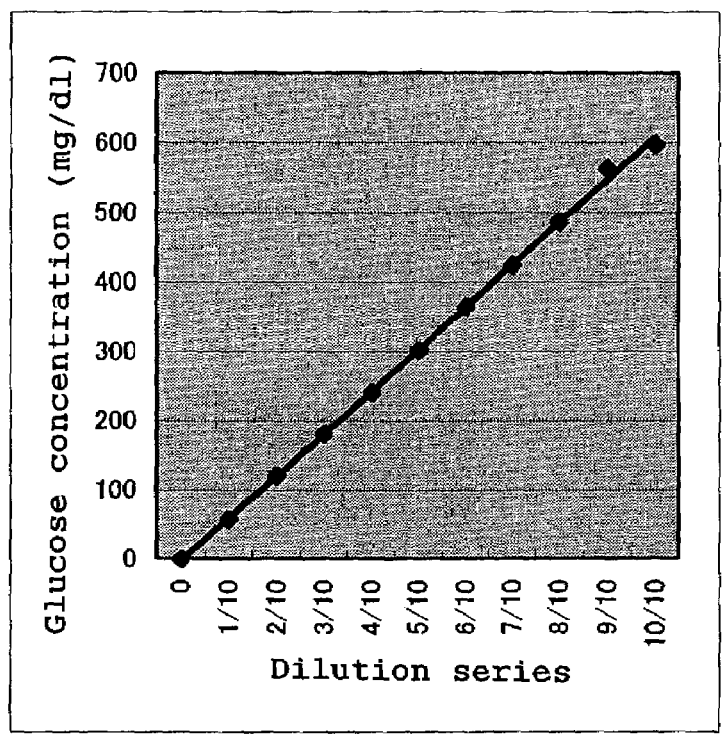
FIG. 2 shows the results of glucose assay.

The results are shown in FIG. 2

Glucose Measurement Methods 300 µl of the reagent was added to 3 µl of the sample, changes in absorbance were calculated for 1 minute beginning two minutes after addition of the reagent, and glucose levels in the samples were calculated based on a two-point calibration curve for purified water and 100 mg/dl glucose standard solution. A Hitachi 7150 automated analyzer was used as the measurement equipment, at a principle wavelength of 480 nm and a measurement temperature of 37° C.

As shown in FIG. 2, good linearity was confirmed in the range of 0-0-600 mg/dl.

Confirmation of Q76K Activity on Maltose

The following reaction reagent was prepared containing 0.45 U/ml of Q76K.

| 50 mM | PIPES-NaOH buffer (pH 6.5) |
|---|---|
| 1 mM | CaCl$_2$ |
| 0.22% | Priton-X100 |
| 0.4 mM | PMS |
| 0.26 mM | WST-1 (Dojin Kagaku) |

Samples were prepared in which 0, 120, 240 and 360 mg/dl of maltose was added to a 100 mg/dl or 300 mg/dl glucose solution. Measurements were performed according to the aforementioned measurement methods for glucose.

Figure 3:
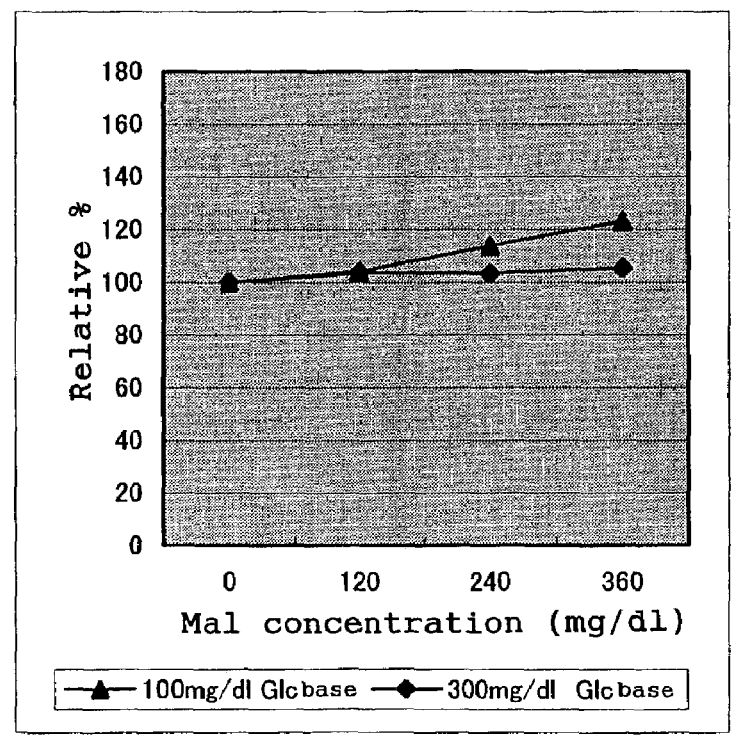
FIG. 3 shows results for activity of Q76K on maltose.

The relative values for the samples containing 100 m/gdl of glucose and various concentration of maltose were evaluated with reference to a value of 100 given for a 100 mg/dl glucose solution containing no maltose. In the same way, the relative values for the samples containing 300 mg/dl of glucose and various concentration of maltose were evaluated with reference to a value of 100 given for a 300 mg/dl glucose solution containing no maltose. The results are shown in FIG. 3.

Confirmation of Q76E Activity on Maltose

Figure 4:
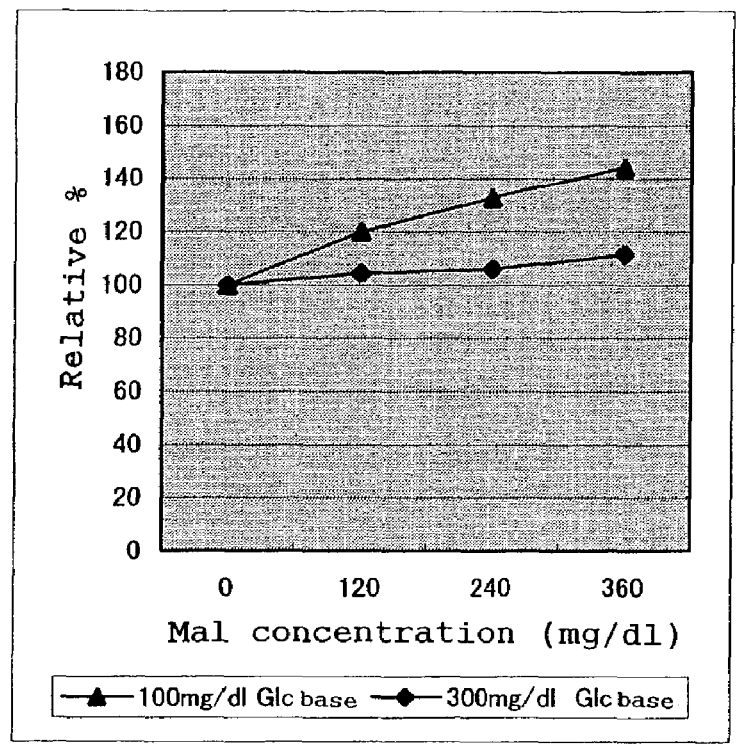
FIG. 4 shows results for activity of Q76E on maltose.

Activity was evaluated using Q76E in the same way as confirmation of Q76K activity on maltose. The enzyme was added at a concentration of 0.24 U/ml. The results are shown in FIG. 4.

Confirmation of Q168V Activity on Maltose

Figure 5:
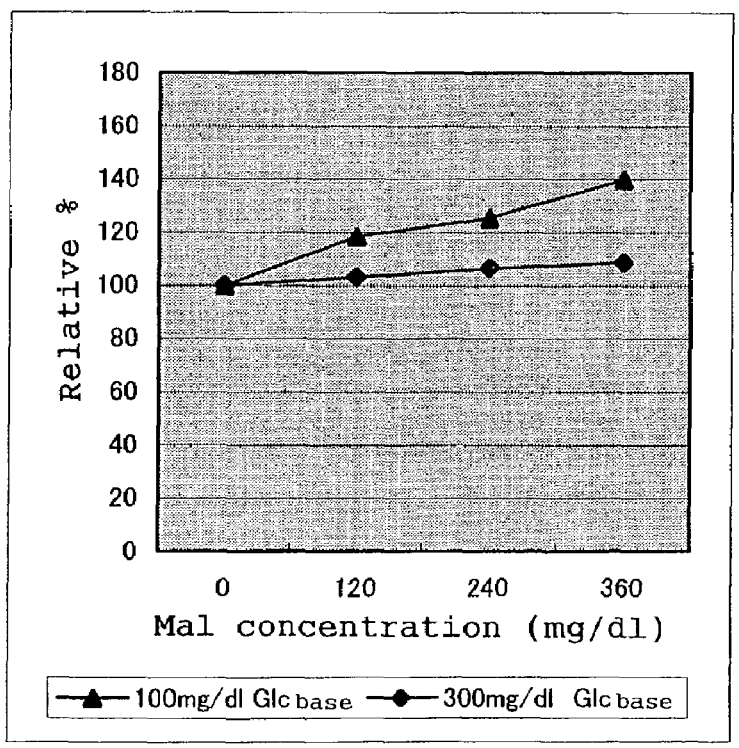
FIG. 5 shows results for activity of Q168V on maltose.

Activity was evaluated using Q168V in the same way as confirmation of Q76K activity on maltose. The enzyme was added at a concentration of 0.35 U/ml. The results are shown in FIG. 5.

Confirmation of Q168A Activity on Maltose

Figure 6:
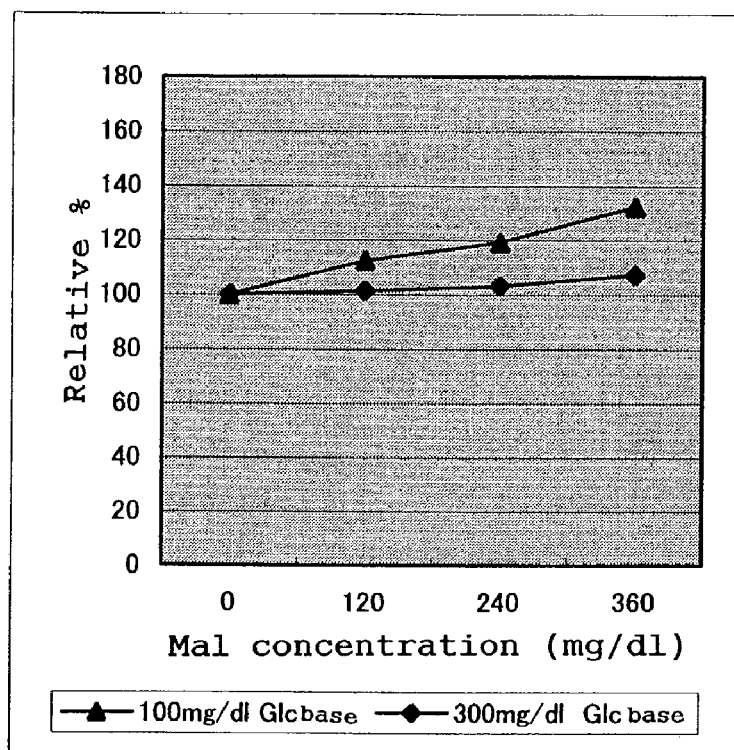
FIG. 6 shows results for activity of Q168A on maltose.

Activity was evaluated using Q168A in the same way as confirmation of Q76K activity on maltose. The enzyme was added at a concentration of 0.6 U/ml The results are shown in FIG. 6.

Confirmation of Wild-type Enzyme Activity on Maltose

Figure 7:
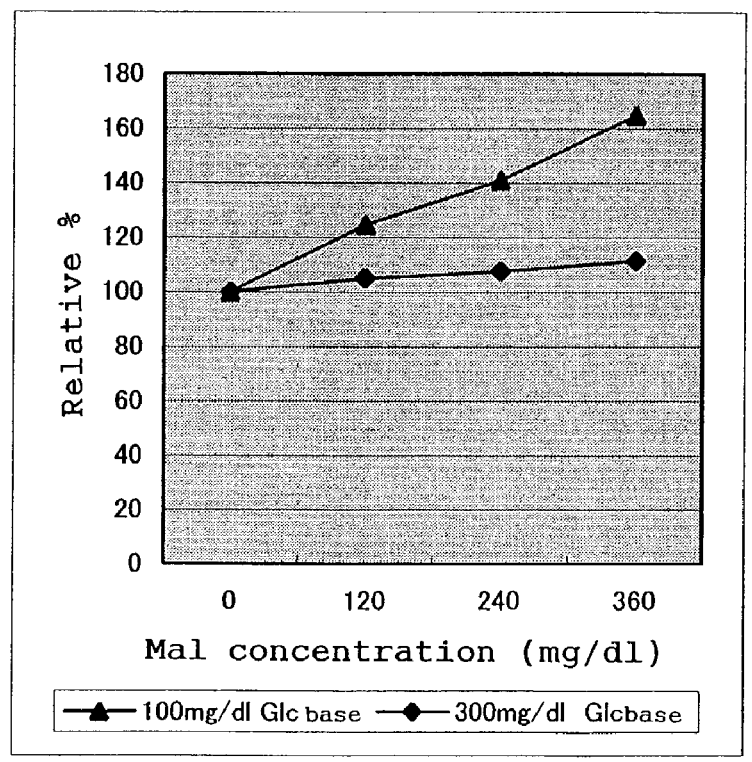
FIG. 7 shows results for activity of the wild-type enzyme on maltose.

Activity was evaluated using the wild-type enzyme in the same way as confirmation of Q76K activity on maltose. The enzyme was added at a concentration of 0.1 U/ml. The results are shown in FIG. 7.

It can be seen from FIGS. 3, 4, 5, 6 and 7 that Q76K, Q76E, Q168V and Q168A have less activity on maltose than the wild-type enzyme.

EXAMPLE 5

Construction and Screening of a Mutation Library

Using expression plasmid pNPG5 as the template, random, mutations were introduced into the 167-169 region of the structural gene by PCR. The PCR reaction was performed in a solution of the composition shown in Table 3 For 2 minutes at 98° C., followed by 30 cycles of 20 seconds at 98° C., 30 seconds at 60° C. and 4 minutes at 72° C.

TABLE 3

| Reagent | Liquid volume |
|---|---|
| KOD Dash DNA Polymerase (2.5 U/µl) | 1.0 µl |
| Template DNA | 1.0 µl |
| Forward primer (SEQ ID No. 12) | 2.5 µl |
| Reverse primer (SEQ ID No. 13) | 2.5 µl |
| 10x buffer | 5.0 µl |
| 2 mM dNTPs | 5.0 µl |
| H$_2$O | 33.0 µl |

The resulting mutation library was transformed into *E. coli* DH5α, and the formed colonies were transplanted to microtitre plates filled with 180 µl/well of LB medium (containing 100 µg/ml of ampicillin and 26 µM of PQQ) and cultured for 24 hours at 37° C. 50 µl of each culture liquid was transferred to a separate microtitre plate, and the cultured cells were broken down by repeated freezing and thawing and centrifuged (2,000 rpm, 10 minutes) to collect the supernatant. Two microtitre plates were filled with 10 µl each of the collected supernatant. One microtitre plate was measured for activity using an activity measuring reagent with glucose as the substrate, and the other microtitre plate was measured for activity using an activity measurement reagent having maltose as the substrate, and the reactions were compared. Several clones were obtained having altered reactivity with respect to maltose.

Those clones having altered reactivity on maltose were cultured in test tubes filled with 5 ml of LB medium (containing 100 µg/ml of ampicillin and 26 µM of PQQ), and confirmation tests showed several of the clones having altered reactivity with respect to maltose.

The results are shown in Table 4.

TABLE 4

| Mutation Site | Activity on Maltose | Mutation Site | Activity on Maltose |
|---|---|---|---|
| N167E + Q168G + L169T | 64% | N167S + Q168N + L169R | 80% |
| Q168G + L169T | 42% | N167G + Q168S + L169Y | 55% |
| N167L + Q168S + L169G | 45% | N167G + Q168S + L169S + L174F + K49N | 39% |
| Q168N + L169N + S189R | 51% | N167E + Q168G + L169A + S189G | 58% |
| N167G + Q168R + L169A | 66% | N167S + Q168G + L169A | 48% |
| N167G + Q168V + L169S | 42% | N167S + Q168V + L169S | 71% |
| N167T + Q168I + L169G | 42% | N167G + Q168W + L169N | 72% |
| N167G + Q168S + L169N | 50% | N167G + Q168S + L169V | 36% |
| Q168R + L169C | 29% | N167S + Q168L + L169G | 41% |
| Q168C + L169S | 33% | N167T + Q168N + L169K | 68% |
| N167G + Q168T + L169A + S207C | 24% | N167A + Q168A + L169P | 63% |
| N167G + Q168S + L169G | 34% | N167G + Q168G | 46% |
| N167G + Q168D + L169K | 35% | Q168P + L169G | 23% |
| N167G + Q168N + L169S | 59% | Q168S + L169G | 22% |
| N188I + T349S | 64% | N167G + Q168G + L169A + F215Y | 32% |
| N167G + Q168T + L169G | 28% | Q168G + L169V | 43% |
| N167G + Q168V + L169T | 43% | N167E + Q168N + L169A | 52% |
| Q168R + L169A | 72% | N167G + Q168R | 23% |
| N167G + Q168T | 69% | N167G + Q168T + L169Q | 72% |
| Q168I + L169G + K300T | 24% | N167G + Q168A | 33% |
| N167T + Q168L + L169K | 63% | N167M + Q168Y + L169G | 60% |
| N167E + Q168S | 32% | N167G + Q168T + L169V + S189G | 42% |
| N167G + Q168G + L169C | 37% | N167G + Q168K + L169D | 41% |
| Q168A + L169D | 16% | Q168S + E245D | 29% |
| Q168S + L169S | 26% | A351T | 74% |
| N167S + Q168S + L169S | 51% | Q168I + L169Q | 51% |
| N167A + Q168S + L169S | 40% | Q168A | 35% |
| Q168S + L169P | 20% | Q168A + L169G | 16% |
| Q168S + L169E | 15% | | |

Mutations were also introduced in the same way in regions 67-69 (forward primer: SEQ ID No. 14, reverse primer: SEQ ID No. 15), 129-131 (forward primer: SEQ ID No. 16, reverse primer: SEQ. ID No. 17), 341-343 (forward primer: SEQ ID No. 18, reverse primer: SEQ ID No. 19). An insertion was also attempted between positions 428 and 429 (forward primer: SEQ ID No. 20, reverse primer: SEQ ID No. 21). The results are shown In Table 5.

TABLE 5

| 67-69 Region | | | |
|---|---|---|---|
| Mutation Site | Activity on maltose | Mutation Site | Activity on maltose |
| P67K + E68K | 79% | P67R + E68R + I69C | 80% |
| P67D + E68T + I69C | 60% | | |

| 129-131 Region | | | |
|---|---|---|---|
| Mutation Site | Activity on maltose | Mutation Site | Activity on maltose |
| E129R + K130G + P131G | 73% | E129Q + K130T + P131R | 80% |
| E129N + P131T | 67% | E129A + K130R + P131K | 70% |

| 341-343 Region | | | |
|---|---|---|---|
| Mutation Site | Activity on maltose | Mutation Site | Activity on maltose |
| E341L + M342P + A343R | 80% | E341S + M342I | 80% |
| A343I | 45% | E341P + M342V + A343C | 50% |
| E341P + M342V + A343R | 76% | E341L + M342R + A343N | 51% |

| Insertion between 428 and 429 | | | |
|---|---|---|---|
| Inserted amino acid | Activity on maltose | Inserted amino acid | Activity on maltose |
| L | 73% | A | 71% |
| K | 79% | | |

Those mutants with greatly reduced activity on maltose were selected (Q168S+E245D, Q168A+L169D, Q168S + L169S, Q168S+L169E, Q168A+L169G, Q168S+L169P), plasmids were extracted from these mutants, *Pseudomonas* was transformed according to the methods described in Examples 3 and 4 to express holoenzymes, and purified enzymes were obtained and their properties were evaluated. The results are shown in Table 6.

TABLE 6

| Mutation | Specific activity | Substrate specificity | Km (Mal) | Km (Glc) | Thermal stability |
|---|---|---|---|---|---|
| Q168S + E245D | 714 | 29% | 24.3 | 14.4 | 55.5% |
| Q16BA + L169D | 106 | 18% | 65.9 | 20.8 | 89.4% |
| Q168S + L169S | 288 | 33% | 55.1 | 14.4 | 83.9% |
| Q168S + L169P | 460 | 25% | 87.1 | 24.1 | 76.3% |
| Q168A + L169G | 170 | 18% | 60.4 | 18.6 | 89.5% |
| Q168S + L169E | 270 | 19% | 70.7 | 8.9 | 63.3% |
| Q168A | 313 | 43% | | | 64.4% |
| Wild type | 1469 | 110% | | | 59.8% |

Note)
Specific activity: Enzyme activity (U/ml)/A280 nm absorbance (ABS)

EXAMPLE 6

Effect of Mutation at Q168 Site on Substrate Specificity

Mutants such as Q168C, Q168D, Q168E, Q168F, Q168G, Q168H, Q168K, Q168L, Q168M, Q168N, Q168P, Q168R, Q168S, Q168T, Q168W and Q168Y were prepared according to the methods disclosed in example 5. Primers used for preparing the mutants are shown in table 7. Further, Table 8 shows the results comparing reactivity of the mutants on maltose by using each mutant in the form of broken cells which were prepared by test tube culture. Mutant enzymes were obtained by extracting plasmids from the mutants, followed by transforming *Pseudomonas* according to the methods described in Examples 3 and 4 to express holoenzymes. The properties of purified enzymes were evaluated. The results are shown in table 9.

TABLE 7

| Mutation site | Forward primer | Reverse primer |
|---|---|---|
| Q168C | SEQ ID No. 22 | SEQ ID No. 23 |
| Q168D | SEQ ID No. 22 | SEQ ID No. 24 |
| Q168E | SEQ ID No. 22 | SEQ ID No. 25 |
| Q168F | SEQ ID No. 22 | SEQ ID No. 26 |
| Q168G | SEQ ID No. 22 | SEQ ID No. 27 |
| Q168H | SEQ ID No. 22 | SEQ ID No. 28 |
| Q168K | SEQ ID No. 22 | SEQ ID No. 29 |
| Q168L | SEQ ID No. 22 | SEQ ID No. 30 |
| Q168M | SEQ ID No. 22 | SEQ ID No. 31 |
| Q168N | SEQ ID No. 22 | SEQ ID No. 32 |
| Q168P | SEQ ID No. 22 | SEQ ID No. 33 |
| Q168R | SEQ ID No. 22 | SEQ ID No. 34 |
| Q168S | SEQ ID No. 22 | SEQ ID No. 35 |
| 0168T | SEQ ID No. 22 | SEQ ID No. 36 |
| Q168W | SEQ ID No. 22 | SEQ ID No. 37 |
| Q168Y | SEQ ID No. 22 | SEQ ID No. 38 |

TABLE 8

| Mutation site | Activity on Maltose | Mutation site | Activity on Maltose |
|---|---|---|---|
| Q168C | 54% | Q168M | 64% |
| Q168D | 29% | Q168N | 82% |
| Q168E | 36% | Q168P | 103% |
| Q168F | 43% | Q168R | 36% |
| Q168G | 46% | Q168S | 60% |
| Q168H | 55% | Q168T | 94% |
| Q168K | 83% | Q168W | 87% |
| Q168L | 92% | Q168Y | 93% |
| Wild type | 104% | | |

TABLE 9

| Mutation | Specific activity | Substrate specificity | Km (Mal) | Km (Glc) | Thermal stability |
|---|---|---|---|---|---|
| Q168C | 55 | 58% | 20.4 | 10.7 | 18.2% |
| Q168D | 102 | 46% | 27.4 | — | 61.4% |
| Q168E | 110 | 51% | 4.7 | 8.6 | 75.4% |
| Q168F | 137 | 52% | 36.4 | 10.3 | 55.5-% |
| Q168G | 667 | 78% | 11.1 | — | 78.7% |
| Q168H | 486 | 58% | 10.2 | 5.4 | 76.0% |
| Q168K | 5 | 80% | 9.6 | 2.2 | — |
| Q168L | 110 | 96% | 8.6 | 4.3 | 37.1% |
| Q168M | 190 | 68% | 22.7 | 5.3 | 78.4% |
| Q168N | 68 | 93% | 3.6 | 4.1 | — |
| Q168P | 128 | 106% | 3.5 | 5.1 | 82.3* |
| Q168R | 57 | 60% | 18.4 | 3.8 | 32.9% |
| Q168S | 483 | 81% | 12.5 | 3.7 | 80.1% |
| Q168T | 11 | 103% | 15.0 | 6.9 | — |
| Q168W | 287 | 96% | 5.3 | 3.2 | 59.2% |
| Q168Y | 297 | 99% | 12.1 | 6.9 | 100.0% |
| Wild type | 1285 | 106% | 3.8 | 6.3 | 52.2% |

Note)
Specific activity: Enzyme activity (U/ml)/A280 nm absorbance (ABS)

Note) Specific activity: Enzyme activity(U/ml)/A280 nm absorbance (ABS)

EXAMPLE 7

Effect of Mutation at L169 Site on Substrate Specificity

Mutants such as L169A, L169V, L169H, L169Y, L169K, L169D, L169S, L169N, L169G and L169C were prepared according to the methods disclosed in example 2. Primers used for preparing the mutants are shown in table 10. Further, table 11 shows the results comparing reactivity of the mutants on maltose by using each mutant in the form of broken cells which were prepared by test tube culture.

TABLE 10

| Mutation site | Forward primer | Reverse primer |
|---|---|---|
| L169A | SEQ ID No.39 | Synthetic oligonucleotide complementary to SEQ ID No.39 |
| L169V | SEQ ID No.40 | Synthetic oligonucleotide complementary to SEQ ID No.40 |
| L169Y | SEQ ID No.41 | Synthetic oligonucleotide complementary to SEQ ID No.41 |
| L169H | SEQ ID No.42 | Synthetic oligonucleotide complementary to SEQ ID No.42 |
| L169K | SEQ ID No.43 | Synthetic oligonucleotide complementary to SEQ ID No.43 |
| L169D | SEQ ID No.44 | Synthetic oligonucleotide complementary to SEQ ID No.44 |
| L169S | SEQ ID No.45 | Synthetic oligonucleotide complementary to SEQ ID No.45 |
| L169N | SEQ ID No.46 | Synthetic oligonucleotide complementary to SEQ ID No.46 |
| L169G | SEQ ID No.47 | Synthetic oligonucleotide complementary to SEQ ID No.47 |
| L169C | SEQ ID No.48 | Synthetic oligonucleotide complementary to SEQ ID No.48 |

TABLE 11

| Mutation site | Activity on Maltose | Mutation site | Activity on Maltose |
|---|---|---|---|
| L169A | 59% | L169D | 38% |
| L169V | 78% | L169S | 57% |
| L169Y | 107% | L169N | 74% |
| L169H | 85% | L169G | 48% |
| L169K | 60% | L169C | 57% |
| Wild type | 97% | | |

EXAMPLE 8

Effect of Combination of Mutations of Q168A Together With L169 Site on Substrate Specificity Mutants such as Q168A+L169A, Q168A+L169C, Q168A+L16.9E, Q168A+L169F, Q168A+L169H, Q168A+L169I, Q168A+L169K, Q168A+L169M, Q168A+L169N, Q168A+L169P, Q168A+L169Q, Q168A+L169R, Q168A+L169S, Q168A+L169T, Q168A+L169V, Q168A+L169W, Q168A+L169Y were prepared according to the methods disclosed in example 5. Primers used for preparing the mutants are shown in table 12. Further, Table 13 shows the results comparing reactivity of the mutants on maltose by using each mutant in the form of broken cells which were prepared by test tube culture. Mutant enzymes were obtained by extracting plasmids from the mutants, followed by transforming

*Pseudomonas* according to the methods described in Examples 3 and 4 to express holoenzymes. The properties of purified enzymes were evaluated. The results are shown in table 14.

TABLE 12

| Mutation site | Forward primer | Reverse primer |
|---|---|---|
| Q168A + L169A | SEQ ID No.12 | SEQ ID No.49 |
| Q168A + L169C | SEQ ID No.12 | SEQ ID No.50 |
| Q168A + L169E | SEQ ID No.12 | SEQ ID No.51 |
| Q168A + L169F | SEQ ID No.12 | SEQ ID No.52 |
| Q168A + L169H | SEQ ID No.12 | SEQ ID No.53 |
| Q168A + L169I | SEQ ID No.12 | SEQ ID No.54 |
| Q168A + L169K | SEQ ID No.12 | SEQ ID No.55 |
| Q168A + L169M | SEQ ID No.12 | SEQ ID No.56 |
| Q168A + L169N | SEQ ID No.12 | SEQ ID No.57 |
| Q168A + L169P | SEQ ID No.12 | SEQ ID No.58 |
| Q168A + L169Q | SEQ ID No.12 | SEQ ID NO.59 |
| Q168A + L169R | SEQ ID No.12 | SEQ ID No.60 |
| Q168A + L169S | SEQ ID No.12 | SEQ ID No.61 |
| Q168A + L169T | SEQ ID No.12 | SEQ ID No.62 |
| Q168A + L169V | SEQ ID No.12 | SEQ ID No.63 |
| Q168A + L169W | SEQ ID No.12 | SEQ ID No.64 |
| Q168A + L169Y | SEQ ID No.12 | SEQ ID No.65 |

TABLE 13

| Mutation site | Activity on maltose | Mutation site | Activity on maltose |
|---|---|---|---|
| Q168A + L169A | 19% | Q168A + L169P | 24% |
| Q168A + L169C | 7% | Q168A + L169Q | 42% |
| Q168A + L169E | 17% | Q168A + L169R | 42% |
| Q168A + L169F | 22% | Q168A + L169S | 14% |
| Q168A + L169H | 21% | Q168A + L169T | 24% |
| Q168A + L169I | 43% | Q168A + L169V | 34% |
| Q168A + L169K | 21% | Q168A + L169W | 33% |
| Q168A + L169M | 22% | Q168A + L169Y | 37% |
| Q168A + L169N | 19% | Wild type | 104% |

TABLE 14

| Mutation | Specific activity | Substrate specificity | Km (Mal) | Km (Glc) | Thermal stability |
|---|---|---|---|---|---|
| Q168A + L169A | 154 | 19% | 126 | 33.0 | 86.2% |
| Q168A + L169C | 63 | 13% | 103 | 35.6 | 100.0% |
| Q168A + L169E | 90 | 19% | 8.6 | 20.4 | 100.0% |
| Q168A + L169F | 138 | 27% | 44.7 | 10.4 | 80.4% |
| Q168A + L169H | 70 | 27% | 99.2 | 15.5 | 100.0% |
| Q168A + L169I | 43 | 53% | 12.5 | 6.0 | 28.7% |
| Q168A + L169K | 129 | 20% | 20.4 | 26.7 | 100.0% |
| Q168A + L169M | 80 | 23% | 52.3 | 15.6 | — |
| Q168A + L169N | 167 | 22% | 59.1 | 34.5 | 83.5% |
| Q168A + L169P | 377 | 24% | 58.0 | 13.9 | 79.9% |
| Q168A + L169Q | 117 | 49% | 156.9 | 5.4 | 100.0% |
| Q168A + L169R | 32 | 45% | 59.0 | 9.6 | 100.0% |
| Q168A + L169S | 42 | 24% | 15.6 | 21.0 | — |
| Q168A + L169T | 98 | 23% | 33.5 | 15.2 | 83.7% |
| Q168A + L169V | 41 | 27% | 49.1 | 24.7 | 40.4% |
| Q168A + L169W | 91 | 38% | 63.3 | 10.8 | 49.4% |
| Q168A + L169Y | 31 | 52% | 13.6 | 11.6 | 74.3% |
| Wild type | 1285 | 106% | 3.8 | 6.3 | 52.2% |

Note)
Specific activity: Enzyme activity (U/ml)/A280 nm absorbance (ABS)

With the present invention it is possible to obtain PQQGDH having improved substrate specificity and thermal stability.

---

What is claimed is:

1. An isolated modified pyrroloquinoline quinone dependent glucose dehydrogenase (PQQGDH), consisting of the amino acid sequence of SEQ ID NO: 2 except that
   (a) the glutamine at position 168 is substituted with an amino acid other than glutamine,
   (b) optionally one or more amino acids at positions selected from the group consisting of positions 67, 68, 69, 76, 89, 167, 169, 341, 342, 343, 351, 49, 174, 188, 189, 207, 215, 245, 300, 349, 129, 130 and 131 of the amino acid sequence of SEQ ID NO: 2 are substituted with a different amino acid than the amino acid in the corresponding position in the amino acid sequence of SEQ ID NO: 2, and
   (c) optionally an amino acid is inserted between positions 428 and 429 of the amino acid sequence of SEQ ID NO: 2,
   wherein the modified PQQGDH has less dehydrogenase activity on maltose than wild-type PQQGDH.

2. The modified PQQGDH according to claim 1, wherein the modified PQQGDH has one or more amino acid substitutions selected from the group consisting of Q76N, Q76E, Q76T, Q76M, Q76G, Q76K, N167E, N167L, N167G, N167T, N167S, N167A, N167M, L169D, L169S, L169W, L169Y, L169A, L169N, L169M, L169V, L169C, L169Q, L169H, L169F, L169R, L169K, L169I, L169T, K89E, K300R, S207C, N188I, T349S, K300T, L174F, K49N, S189G, F215Y, S189G, E245D, A351T, P67K, E68K, P67D, E68T, I69C, P67R, E68R, E129R, K130G, P131G, E129N, P131T, E129Q, K130T, P131R, E129A, K130R, P131K, E341L, M342P, A343R, A343I, E341P, M342V, E341S, M342I, A343C, M342R, A343N, L169P, L169G, and L169E.

3. The modified PQQGDH according to claim 1, wherein the modified PQQGDH has an amino acid substitution selected from the group consisting of (Q168A+L169D), (Q168S+L169S), (N167E+Q168G+L169T), (N167S+Q168N+L169R), (Q168G+L169T), (N167G+Q168S+L169Y), (N167L+Q168S+L169G), (N167G+Q168S+L169S+L174F+K49N), (Q168N+L169N+S189R), (N167E+Q168G+L169A+S189G), (N167G+Q168R+L169A), (N167S+Q168G+L169A), (N167G+Q168V+L169S), (N167S+Q168V+L169S), (N167T+Q168I+L169G), (N167G+Q168W+L169N), (N167G+Q168S+L169N), (N167G+Q168S+L169V), (Q168R+L169C), (N167S+Q168L+L169G), (Q168C+L169S), (N167T+Q168N+L169K), (N167G+Q168T+L169A+S207C), (N167A+Q168A+L169P), (N167G+Q168S+L169G), (N167G+Q168G), (N167G+Q168D+L169K), (Q168P+L169G), (N167G+Q168N+L169S), (Q168S+L169G), (N167G+Q168G+L169A+F215Y), (N167G+Q168T+L169G), (Q168G+L169V), (N167G+Q168V+L169T), (N167E+Q168N+L169A), (Q168R+L169A), (N167G+Q168R), (N167G+Q168T), (N167G+Q168T+L169Q), (Q168I+L169G+K300T), (N167G+Q168A), (N167T+Q168L+L169K), (N167M+Q168Y+L169G), (N167E+Q168S), (N167G+Q168T+L169V+S189G), (N167G+Q168G+L169C), (N167G+Q168K+L169D), (Q168A+L169D), (Q168S+E245D), (Q168S+L169S), (N167S+Q168S+L169S), (Q168I+L169Q), (N167A+Q168S+L169S), (Q168S+L169E), (Q168A+L169G), (Q168S+L169P), (Q168A+L169A), (Q168A+L169C), (Q168A+L169E), (Q168A+L169F), (Q168A+L169H), (Q168A+L169I), (Q168A+L169K), (Q168A+L169M), (Q168A+L169N), (Q168A+L169P), (Q168A+L169Q), (Q168A+L169R), (Q168A+L169S), (Q168A+L169T), (Q168A+L169V), (Q168A+L169W), and (Q168A+L169Y).

4. The modified PQQGDH according to claim 1, wherein the amino acid substitution at position 168 is selected from the group consisting of Q168I, Q168V, Q168C, Q168D, Q168E, Q168F, Q168G, Q168H, Q168K, Q168L, Q168M, Q168N, Q168R, Q168S, and Q168W.

5. The modified PQQGDH according to claim 4, wherein the modified PQQGDH has one or more amino acid substitutions selected from the group consisting of Q76N, Q76E, Q76T, Q76M, Q76G, Q76K, N167E, N167L, N167G, N167T, N167S, N167A, N167M, L169D, L169S, L169W, L169Y, L169A, L169N, L169M, L169V, L169C, L169Q, L169H, L169F, L169R, L169K, L169I, L169T, K89E, K300R, S207C, N188I, T349S, K300T, L174F, K49N, S189G, F215Y, S189G, E245D, A351T, P67K, E68K, P67D, E68T, I69C, P67R, E68R, E129R, K130G, P131G, E129N, P131T, E129Q, K130T, P131R, E129A, K130R, P131K, E341L, M342P, A343R, A343I, E341P, M342V, E341S, M342I, A343C, M342R, A343N, L169P, L169G, and L169E.

6. The modified PQQGDH according to claim 1, wherein the amino acid substitution at position 168 is Q168A.

7. The modified PQQGDH according to claim 6, wherein the modified PQQGDH has one or more amino acid substitutions selected from the group consisting of Q76N, Q76E, Q76T, Q76M, Q76G, Q76K, N167E, N167L, N167G, N167T, N167S, N167A, N167M, L169D, L169S, L169W, L169Y, L169A, L169N, L169M, L169V, L169C, L169Q, L169H, L169F, L169R, L169K, L169I, L169T, K89E, K300R, S207C, N188I, T349S, K300T, L174F, K49N, S189G, F215Y, S189G, E245D, A351T, P67K, E68K, P67D, E68T, I69C, P67R, E68R, E129R, K130G, P131G, E129N, P131T, E129Q, K130T, P131R, E129A, K130R, P131K, E341L, M342P, A343R, A343I, E341P, M342V, E341S, M342I, A343C, M342R, A343N, L169P, L169G, and L169E.

8. The modified PQQGDH according to claim 1, wherein one or more one or more amino acids at positions selected from the group consisting of positions 67, 68, 69, 76, 89, 167, 169, 341, 342, 343, 351, 49, 174, 188, 189, 207, 215, 245, 300, 349, 129, 130 and 131 of the amino acid sequence of SEQ ID NO: 2 are substituted with a different amino acid than the amino acid in the corresponding position in the amino acid sequence of SEQ ID NO: 2.

9. The modified PQQGDH according to claim 8, wherein the amino acid substitution at position 168 is selected from the group consisting of Q168I, Q168V, Q168C, Q168D, Q168E, Q168F, Q168G, Q168H, Q168K, Q168L, Q168M, Q168N, Q168R, Q168S, and Q168W.

10. The modified PQQGDH according to claim 8, wherein the amino acid substitution at position 168 is Q168A.

11. The modified PQQGDH according to claim 1, wherein an amino acid is inserted between positions 428 and 429 of the amino acid sequence of SEQ ID NO: 2.

12. The modified PQQGDH according to claim 11, wherein the amino acid substitution at position 168 is selected from the group consisting of Q168I, Q168V, Q168C, Q168D, Q168E, Q168F, Q168G, Q168H, Q168K, Q168L, Q168M, Q168N, Q168R, Q168S, and Q168W.

13. The modified PQQGDH according to claim 11, wherein the amino acid substitution at position 168 is Q168A.

14. A method for determining glucose concentration in a sample using the modified PQQGDH of claim 1.

* * * * *

SEQUENCE LISTING

```
<160> NUMBER OF SEQ ID NOS: 68
<210> SEQ ID NO 1
<211> LENGTH: 1368
<212> TYPE: DNA
<213> ORGANISM: Acinetobacter baumannii

<400> SEQUENCE: 1 gatataccto tgcacctgc tcagttcgca aaagcgaaaa cagaaaattt tgataaaaaa      60
gtgattctgt ccaatttaaa taaaccacat gctttgttat gggggccaga taatcaaatt    120
tggttaaccg aacgtgcaac tggcaaaatt ttaagagtaa atcctgtatc tggtagcgcg    180
aaaacagtat ttcaggttcc tgaaattgtg agtgatgctg atgggcaaaa tggtttgtta    240
ggttttgctt ttcatcctga cttttaaacat aaccctttata tctatattttc aggcactttt    300 aaaaatccaa aatctacaga taaagagtta cctaatcaga cgattattcg tagatatacc    360
tataataaaa ctacagatac atttgaaaag cctattgatt tgattgcagg tttaccgtca    420
tcaaaagatc atcagtctgg tcgtctcgtt attggtccag accaaaaaat ctactatacg    480
attggtgacc aaggtcgtaa tcagttagct tatctgttct taccgaatca ggcacagcat    540
actccgactc agcaagagct caatagtaaa gactaccata catatatggg taaagtatta    600
cgcttaaatc tggacggcag tgtacctaaa gacaacccaa gctttaacgg cgtagtgagt    660
catatctaca ctttagggca ccgtaatcca caaggtttag catttgcccc aaatggaaag    720
```

-continued

```
cttttacaat ctgagcaagg accaaattct gatgatgaaa ttaaccttgt attaaaaggt      780
ggtaactatg gctggccaaa tgtagctggt tataaagatg acagtggtta tgcctatgca      840
aactattcgg cagcaaccaa taatcacaa attaaagatt tagctcaaaa cgggataaaa       900
gtagcaacag tgttcctgt gactaaagag tctgaatgga ctggtaaaaa ctttgtgccg       960
cctttgaaaa ctttatatac ggtacaagat acctataact ataatgaccc tacttgtggt     1020
gagatggcat atatttgctg ccaacggtt gcaccgtcat cagcatatgt atatacggga     1080
ggcaaaaaag cgattccagg gtgggaaaat acattattgg tcccatcttt aaaacgtggg    1140
gtgattttcc gtattaaatt ggacccgaca tatagcacga ctttggatga tgctatccca    1200
atgtttaaaa gcaataaccg ttatcgtgat gtcatcgcta gtccagaagg taataccta     1260 tatgtgctga ctgatacagc ggggaatgta caaaaagatg atggttctgt cactcatact    1320
ttagagaatc ccggttctct cattaaattt acatataacg gtaagtaa                 1368
```

<210> SEQ ID NO 2
<211> LENGTH: 455
<212> TYPE: PRT
<213> ORGANISM: Acinetobacter baumannii

<400> SEQUENCE: 2

```
Asp Ile Pro Leu Thr Pro Ala Gln Phe Ala Lys Ala Lys Thr Glu Asn
1               5                   10                  15

Phe Asp Lys Lys Val Ile Leu Ser Asn Leu Asn Lys Pro His Ala Leu
                20                  25                  30

Leu Trp Gly Pro Asp Asn Gln Ile Trp Leu Thr Glu Arg Ala Thr Gly
            35                  40                  45

Lys Ile Leu Arg Val Asn Pro Val Ser Gly Ser Ala Lys Thr Val Phe
        50                  55                  60

Gln Val Pro Glu Ile Val Ser Asp Ala Asp Gly Gln Asn Gly Leu Leu
65                  70                  75                  80

Gly Phe Ala Phe His Pro Asp Phe Lys His Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Thr Thr Asp Thr Phe
        115                 120                 125

Glu Lys Pro Ile Asp Leu Ile Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Ser Lys Asp Tyr
            180                 185                 190

His Thr Tyr Met Gly Lys Val Leu Arg Leu Asn Leu Asp Gly Ser Val
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Ala Pro Asn Gly Lys
225                 230                 235                 240

Leu Leu Gln Ser Glu Gln Gly Pro Asn Ser Asp Asp Glu Ile Asn Leu
                245                 250                 255

Val Leu Lys Gly Gly Asn Tyr Gly Trp Pro Asn Val Ala Gly Tyr Lys
```

-continued

```
                260                 265                 270
Asp Asp Ser Gly Tyr Ala Tyr Ala Asn Tyr Ser Ala Thr Asn Lys
        275                 280                 285

Ser Gln Ile Lys Asp Leu Ala Gln Asn Gly Ile Lys Val Ala Thr Gly
    290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335

Pro Thr Cys Gly Glu Met Ala Tyr Ile Cys Trp Pro Thr Val Ala Pro
            340                 345                 350

Ser Ser Ala Tyr Val Tyr Thr Gly Gly Lys Lys Ala Ile Pro Gly Trp
        355                 360                 365

Glu Asn Thr Leu Leu Val Pro Ser Leu Lys Arg Gly Val Ile Phe Arg
    370                 375                 380

Ile Lys Leu Asp Pro Thr Tyr Ser Thr Thr Leu Asp Asp Ala Ile Pro
385                 390                 395                 400

Met Phe Lys Ser Asn Asn Arg Tyr Arg Asp Val Ile Ala Ser Pro Glu
                405                 410                 415

Gly Asn Thr Leu Tyr Val Leu Thr Asp Thr Ala Gly Asn Val Gln Lys
            420                 425                 430

Asp Asp Gly Ser Val Thr His Thr Leu Glu Asn Pro Gly Ser Leu Ile
        435                 440                 445

Lys Phe Thr Tyr Asn Gly Lys
    450                 455

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
agtgatgctg atgggaataa tggtttgtta ggt                                    33

<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
agtgatgctg atggggagaa tggtttgtta ggt                                    33

<210> SEQ ID NO 5
<211> LENGTH: 33
<212> TYPE: DNA
<213> ORGANISM: Artificial Sequence
<220> FEATURE:
<223> OTHER INFORMATION: Synthetic

<400> SEQUENCE: 5
agtgatgctg atgggacaaa tggtttgtta ggt                                    33

<210> SEQ ID NO 6
<211> LENGTH: 33
<212> TYPE: DNA
<213> ORGANISM: Artificial Sequence
```

```
<220> FEATURE:
<223> OTHER INFORMATION: Synthetic

<400> SEQUENCE: 6
agtgatgctg atgggatgaa tggtttgtta ggt                              33

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
agtgatgctg atgggggaa tggtttgtta ggt                               33

<210> SEQ ID NO 8
<211> LENGTH: 33
<212> TYPE: DNA
<213> ORGANISM: Artificial Sequence
<220> FEATURE:
<223> OTHER INFORMATION: Synthetic

<400> SEQUENCE: 8
agtgatgctg atgggaagaa tggtttgtta ggt                              33

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
gaccaaggtc gtaatatttt agcttatctg ttc                              33

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
gaccaaggtc gtaatgtatt agcttatctg ttc                              33

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
gaccaaggtc gtaatgcatt agcttatctg ttc                              33

<210> SEQ ID NO 12
<211> LENGTH: 43
<212> TYPE: DNA
<213> ORGANISM: Artificial Sequence
<220> FEATURE:
<223> OTHER INFORMATION: Synthetic

<400> SEQUENCE: 12
cgaatcaggc acagcatact ccgactcagc aagagctcaa tag                   43
```

```
<210> SEQ ID NO 13
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(25)
<223> OTHER INFORMATION: page 41, table 3

<400> SEQUENCE: 13
gtaagaacag ataagcnnnn nnnnnacgac cttggtcacc aatcg            45

<210> SEQ ID NO 14
<211> LENGTH: 40
<212> TYPE: DNA
<213> ORGANISM: Artificial Sequence
<220> FEATURE:
<223> OTHER INFORMATION: Synthetic

<400> SEQUENCE: 14
gatgctgatg ggcaaaatgg tttgttaggt tttgcttttc                  40

<210> SEQ ID NO 15
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(15)
<223> OTHER INFORMATION: page 43, line 3 from the bottom

<400> SEQUENCE: 15
actcacnnnn nnnnnaacct gaaatactgt tttcgcgc                    38

<210> SEQ ID NO 16
<211> LENGTH: 50
<212> TYPE: DNA
<213> ORGANISM: Artificial Sequence
<220> FEATURE:
<223> OTHER INFORMATION: Sythetic

<400> SEQUENCE: 16
tttaccgtca tcaaaagatc atcagtctgg tcgtctcgtt attggtccag       50

<210> SEQ ID NO 17
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(26)
<223> OTHER INFORMATION: page 43, line 2 from the bottom

<400> SEQUENCE: 17
cctgcaatca aatcaatnnn nnnnnnaaat gtatctgtag ttttattata gg    52

<210> SEQ ID NO 18
<211> LENGTH: 39
<212> TYPE: DNA
<213> ORGANISM: Artificial Sequence
<220> FEATURE:
<223> OTHER INFORMATION: Synthetic
```

<400> SEQUENCE: 18
acggttgcac cgtcatcagc atatgtatat acgggaggc                                    39

<210> SEQ ID NO 19
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(24)
<223> OTHER INFORMATION: page 43, the bottom line

<400> SEQUENCE: 19
tggccagcaa atatannnnn nnnnaccaca agtagggtc                                    39

<210> SEQ ID NO 20
<211> LENGTH: 34
<212> TYPE: DNA
<213> ORGANISM: Artificial Sequence
<220> FEATURE:
<223> OTHER INFORMATION: Synthetic

<400> SEQUENCE: 20
atggttctgt cactcatact ttagagaatc ccgg                                         34

<210> SEQ ID NO 21
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(19)
<223> OTHER INFORMATION: page 44, lines 2-3

<400> SEQUENCE: 21 catcttttg tacattnnnc cccgctgtat cagtc                                         35

<210> SEQ ID NO 22
<211> LENGTH: 33
<212> TYPE: DNA
<213> ORGANISM: Artificial Sequence
<220> FEATURE:
<223> OTHER INFORMATION: Synthetic

<400> SEQUENCE: 22
ttaccgaatc aggcacagca tactccgact cag                                          33

<210> SEQ ID NO 23
<211> LENGTH: 33
<212> TYPE: DNA
<213> ORGANISM: Artificial Sequence
<220> FEATURE:
<223> OTHER INFORMATION: Synthetic

<400> SEQUENCE: 23
gaacagataa gctaagcaat tacgaccttg gtc                                          33

<210> SEQ ID NO 24
<211> LENGTH: 33
<212> TYPE: DNA
<213> ORGANISM: Artificial Sequence
<220> FEATURE:

```
<223> OTHER INFORMATION: Synthetic

<400> SEQUENCE: 24
gaacagataa gctaartcat tacgaccttg gtc                         33

<210> SEQ ID NO 25
<211> LENGTH: 33
<212> TYPE: DNA
<213> ORGANISM: Artificial Sequence
<220> FEATURE:
<223> OTHER INFORMATION: Synthetic

<400> SEQUENCE: 25
gaacagataa gctaaytcat tacgaccttg gtc                         33

<210> SEQ ID NO 26
<211> LENGTH: 33
<212> TYPE: DNA
<213> ORGANISM: Artificial Sequence
<220> FEATURE:
<223> OTHER INFORMATION: Synthetic

<400> SEQUENCE: 26
gaacagataa gctaaraaat tacgaccttg gtc                         33

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27
gaacagataa gctaagccat tacgaccttg gtc                         33

<210> SEQ ID NO 28
<211> LENGTH: 33
<212> TYPE: DNA
<213> ORGANISM: Artificial Sequence
<220> FEATURE:
<223> OTHER INFORMATION: Synthetic

<400> SEQUENCE: 28
gaacagataa gctaartgat tacgaccttg gtc                         33

<210> SEQ ID NO 29
<211> LENGTH: 33
<212> TYPE: DNA
<213> ORGANISM: Artificial Sequence
<220> FEATURE:
<223> OTHER INFORMATION: Synthetic

<400> SEQUENCE: 29
gaacagataa gctaayttat tacgaccttg gtc                         33

<210> SEQ ID NO 30
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: page 46, table 7

<400> SEQUENCE: 30
```

-continued gaacagataa gctaanagat tacgaccttg gtc     33

<210> SEQ ID NO 31
<211> LENGTH: 33
<212> TYPE: DNA
<213> ORGANISM: Artificial Sequence
<220> FEATURE:
<223> OTHER INFORMATION: Synthetic

<400> SEQUENCE: 31
gaacagataa gctaacatat tacgaccttg gtc     33

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
gaacagataa gctaarttat tacgaccttg gtc     33

<210> SEQ ID NO 33
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: page 46, table 7

<400> SEQUENCE: 33
gaacagataa gctaanggat tacgaccttg gtc     33

<210> SEQ ID NO 34
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: page 44, table 7

<400> SEQUENCE: 34
gaacagataa gctaancgat tacgaccttg gtc     33

<210> SEQ ID NO 35
<211> LENGTH: 33
<212> TYPE: DNA
<213> ORGANISM: Artificial Sequence
<220> FEATURE:
<223> OTHER INFORMATION: Synthetic

<400> SEQUENCE: 35
gaacagataa gctaagctat tacgaccttg gtc     33

<210> SEQ ID NO 36
<211> LENGTH: 33
<212> TYPE: DNA
<213> ORGANISM: Artificial Sequence
<220> FEATURE:
<223> OTHER INFORMATION: Synthetic

```
<400> SEQUENCE: 36
gaacagataa gctaacgtat tacgaccttg gtc                               33

<210> SEQ ID NO 37
<211> LENGTH: 33
<212> TYPE: DNA
<213> ORGANISM: Artificial Sequence
<220> FEATURE:
<223> OTHER INFORMATION: Synthetic

<400> SEQUENCE: 37
gaacagataa gctaaccaat tacgaccttg gtc                               33

<210> SEQ ID NO 38
<211> LENGTH: 33
<212> TYPE: DNA
<213> ORGANISM: Artificial Sequence
<220> FEATURE:
<223> OTHER INFORMATION: Synthetic

<400> SEQUENCE: 38
gaacagataa gctaartaat tacgaccttg gtc                               33

<210> SEQ ID NO 39
<211> LENGTH: 39
<212> TYPE: DNA
<213> ORGANISM: Artificial Sequence
<220> FEATURE:
<223> OTHER INFORMATION: Synthetic

<400> SEQUENCE: 39
gaccaaggtc gtaatcaggc agcttatctg ttcttaccg                         39

<210> SEQ ID NO 40
<211> LENGTH: 39
<212> TYPE: DNA
<213> ORGANISM: Artificial Sequence
<220> FEATURE:
<223> OTHER INFORMATION: Synthetic

<400> SEQUENCE: 40
gaccaaggtc gtaatcaggt tgcttatctg ttcttaccg                         39

<210> SEQ ID NO 41
<211> LENGTH: 39
<212> TYPE: DNA
<213> ORGANISM: Artificial Sequence
<220> FEATURE:
<223> OTHER INFORMATION: Synthetic

<400> SEQUENCE: 41
gaccaaggtc gtaatcagta tgcttatctg ttcttaccg                         39

<210> SEQ ID NO 42
<211> LENGTH: 39
<212> TYPE: DNA
<213> ORGANISM: Artificial Sequence
<220> FEATURE:
<223> OTHER INFORMATION: Synthetic

<400> SEQUENCE: 42
gaccaaggtc gtaatcagca tgcttatctg ttcttaccg                         39

<210> SEQ ID NO 43
<211> LENGTH: 39
```

```
<212> TYPE: DNA
<213> ORGANISM: Artificial Sequence
<220> FEATURE:
<223> OTHER INFORMATION: Synthetic

<400> SEQUENCE: 43
gaccaaggtc gtaatcagaa agcttatctg ttcttaccg                                39

<210> SEQ ID NO 44
<211> LENGTH: 39
<212> TYPE: DNA
<213> ORGANISM: Artificial Sequence
<220> FEATURE:
<223> OTHER INFORMATION: Synthetic

<400> SEQUENCE: 44
gaccaaggtc gtaatcagga tgcttatctg ttcttaccg                                39

<210> SEQ ID NO 45
<211> LENGTH: 39
<212> TYPE: DNA
<213> ORGANISM: Artificial Sequence
<220> FEATURE:
<223> OTHER INFORMATION: Synthetic

<400> SEQUENCE: 45
gaccaaggtc gtaatcagtc agcttatctg ttcttaccg                                39

<210> SEQ ID NO 46
<211> LENGTH: 39
<212> TYPE: DNA
<213> ORGANISM: Artificial Sequence
<220> FEATURE:
<223> OTHER INFORMATION: Synthetic

<400> SEQUENCE: 46
gaccaaggtc gtaatcagaa tgcttatctg ttcttaccg                                39

<210> SEQ ID NO 47
<211> LENGTH: 39
<212> TYPE: DNA
<213> ORGANISM: Artificial Sequence
<220> FEATURE:
<223> OTHER INFORMATION: Synthetic

<400> SEQUENCE: 47
gaccaaggtc gtaatcaggg agcttatctg ttcttaccg                                39

<210> SEQ ID NO 48
<211> LENGTH: 39
<212> TYPE: DNA
<213> ORGANISM: Artificial Sequence
<220> FEATURE:
<223> OTHER INFORMATION: Synthetic

<400> SEQUENCE: 48
gaccaaggtc gtaatcagtg tgcttatctg ttcttaccg                                39

<210> SEQ ID NO 49
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
```

```
<223> OTHER INFORMATION: page 49, table 12

<400> SEQUENCE: 49
gtaagaacag ataagcngat gcattacgac cttggtcacc aatcg          45

<210> SEQ ID NO 50
<211> LENGTH: 45
<212> TYPE: DNA
<213> ORGANISM: Artificial Sequence
<220> FEATURE:
<223> OTHER INFORMATION: Synthetic

<400> SEQUENCE: 50
gtaagaacag ataagcrcat gcattacgac cttggtcacc aatcg          45

<210> SEQ ID NO 51
<211> LENGTH: 45
<212> TYPE: DNA
<213> ORGANISM: Artificial Sequence
<220> FEATURE:
<223> OTHER INFORMATION: Synthetic

<400> SEQUENCE: 51
gtaagaacag ataagcytct gcattacgac cttggtcacc aatcg          45

<210> SEQ ID NO 52
<211> LENGTH: 45
<212> TYPE: DNA
<213> ORGANISM: Artificial Sequence
<220> FEATURE:
<223> OTHER INFORMATION: Synthetic

<400> SEQUENCE: 52
gtaagaacag ataagcraat gcattacgac cttggtcacc aatcg          45

<210> SEQ ID NO 53
<211> LENGTH: 45
<212> TYPE: DNA
<213> ORGANISM: Artificial Sequence
<220> FEATURE:
<223> OTHER INFORMATION: Synthetic

<400> SEQUENCE: 53
gtaagaacag ataagcrtgt gcattacgac cttggtcacc aatcg          45

<210> SEQ ID NO 54
<211> LENGTH: 45
<212> TYPE: DNA
<213> ORGANISM: Artificial Sequence
<220> FEATURE:
<223> OTHER INFORMATION: Synthetic

<400> SEQUENCE: 54
gtaagaacag ataagcdatt gcattacgac cttggtcacc aatcg          45

<210> SEQ ID NO 55
<211> LENGTH: 45
<212> TYPE: DNA
<213> ORGANISM: Artificial Sequence
<220> FEATURE:
<223> OTHER INFORMATION: Synthetic

<400> SEQUENCE: 55
gtaagaacag ataagcyttt gcattacgac cttggtcacc aatcg          45
```

```
<210> SEQ ID NO 56
<211> LENGTH: 45
<212> TYPE: DNA
<213> ORGANISM: Artificial Sequence
<220> FEATURE:
<223> OTHER INFORMATION: Synthetic

<400> SEQUENCE: 56
gtaagaacag ataagccatt gcattacgac cttggtcacc aatcg          45

<210> SEQ ID NO 57
<211> LENGTH: 45
<212> TYPE: DNA
<213> ORGANISM: Artificial Sequence
<220> FEATURE:
<223> OTHER INFORMATION: Synthetic

<400> SEQUENCE: 57
gtaagaacag ataagcrttt gcattacgac cttggtcacc aatcg          45

<210> SEQ ID NO 58
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: page 49, table 12

<400> SEQUENCE: 58
gtaagaacag ataagcnggt gcattacgac cttggtcacc aatcg          45

<210> SEQ ID NO 59
<211> LENGTH: 45
<212> TYPE: DNA
<213> ORGANISM: Artificial Sequence
<220> FEATURE:
<223> OTHER INFORMATION: Synthetic

<400> SEQUENCE: 59
gtaagaacag ataagcytgt gcattacgac cttggtcacc aatcg          45

<210> SEQ ID NO 60
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: page 49, table 12

<400> SEQUENCE: 60
gtaagaacag ataagcncgt gcattacgac cttggtcacc aatcg          45

<210> SEQ ID NO 61
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: page 49, table 12
```

```
<400> SEQUENCE: 61
gtaagaacag ataagcngat gcattacgac cttggtcacc aatcg         45

<210> SEQ ID NO 62
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: page 49, table 12

<400> SEQUENCE: 62
gtaagaacag ataagcngtt gcattacgac cttggtcacc aatcg         45

<210> SEQ ID NO 63
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: page 49, table 12

<400> SEQUENCE: 63
gtaagaacag ataagcnact gcattacgac cttggtcacc aatcg         45

<210> SEQ ID NO 64
<211> LENGTH: 45
<212> TYPE: DNA
<213> ORGANISM: Artificial Sequence
<220> FEATURE:
<223> OTHER INFORMATION: Synthetic

<400> SEQUENCE: 64
gtaagaacag ataagcccat gcattacgac cttggtcacc aatcg         45

<210> SEQ ID NO 65
<211> LENGTH: 45
<212> TYPE: DNA
<213> ORGANISM: Artificial Sequence
<220> FEATURE:
<223> OTHER INFORMATION: Synthetic

<400> SEQUENCE: 65
gtaagaacag ataagcrtat gcattacgac cttggtcacc aatcg         45

<210> SEQ ID NO 66
<211> LENGTH: 36
<212> TYPE: DNA
<213> ORGANISM: Artificial Sequence
<220> FEATURE:
<223> OTHER INFORMATION: Synthetic

<400> SEQUENCE: 66
gaccaaggtc gtaatagtga ggcttatctg ttctta                   36

<210> SEQ ID NO 67
<211> LENGTH: 36
<212> TYPE: DNA
<213> ORGANISM: Artificial Sequence
<220> FEATURE:
<223> OTHER INFORMATION: Synthetic
```

```
<400> SEQUENCE: 67
gaccaaggtc gtaatagtcc cgcttatctg ttctta                                36

<210> SEQ ID NO 68
<211> LENGTH: 36
<212> TYPE: DNA
<213> ORGANISM: Artificial Sequence
<220> FEATURE:
<223> OTHER INFORMATION: Synthetic

<400> SEQUENCE: 68
gaccaaggtc gtaatgcagg cgcttatctg ttctta                                36
```